(12) United States Patent
Inoue

(10) Patent No.: US 7,732,208 B2
(45) Date of Patent: Jun. 8, 2010

(54) METHOD OF CONDUCTING HOMOLOGOUS RECOMBINATION

(75) Inventor: Hirokazu Inoue, Saitama (JP)

(73) Assignee: National University Corporation Saitama University, Saitama (JP)

( * ) Notice: Subject to any disclaimer, the term of this patent is extended or adjusted under 35 U.S.C. 154(b) by 732 days.

(21) Appl. No.: 10/590,441

(22) PCT Filed: Aug. 31, 2004

(86) PCT No.: PCT/JP2004/012516

§ 371 (c)(1),
(2), (4) Date: Aug. 23, 2006

(87) PCT Pub. No.: WO2005/083090

PCT Pub. Date: Sep. 9, 2005

(65) Prior Publication Data

US 2008/0138905 A1 Jun. 12, 2008

(30) Foreign Application Priority Data

Feb. 27, 2004 (JP) .............................. 2004-052952

(51) Int. Cl.
*C12N 15/80* (2006.01)
*C12N 1/15* (2006.01)
(52) U.S. Cl. .................. 435/471; 435/254.3; 435/254.4
(58) Field of Classification Search .................. None
See application file for complete search history.

(56) References Cited

U.S. PATENT DOCUMENTS

2004/0073967 A1* 4/2004 Hooykaas et al. ........... 800/278

FOREIGN PATENT DOCUMENTS

| JP | 2001-046053 | 2/2001 |
|---|---|---|
| JP | 2003526376 A | 9/2003 |
| WO | 01068882 A2 | 9/2001 |

OTHER PUBLICATIONS

Ninomiya et al., PNAS, 101, 33, 12248-12253, 2004.*
Ninimiya et al. Genes and Genetic Systems, Dec. 2003, vol. 78, No. 6, p. 463.*

Terada, Rie, et al., Efficient gene targeting by homologous recombination in rice, Nature Biotechnology, vol. 20, Oct. 2002, pp. 1030-1034.
Jeannotte, Lucie, et al., Low level of Hox1.3 gene expression does not preclude the use of promoterless vectors to generate a targeted gene disruption, Molecular and Cellular Biology, vol. 11, No. 11, Nov. 1991, pp. 5578-5585.
Gallego, M.E., et al., Ku80 plays a role in non-homologous recombination but is not required for T-DNA integration in Arabidopsis, The Plant Journal, (2003) 35: 557-565.
Walker, John R., et al., Structure of the Ku heterodimer bound to DNA and its implications for double-strand break repair, Nature, vol. 412, Aug. 9, 2001, pp. 607-614.
Critchlow, Susan E., et al., DNA end-joining: from yeast to man, TIBS 23, Oct. 1998, pp. 394-398.
Pierce, Andrew J., et al., Ku DNA end-binding protein modulates homologous repair of double-strand breaks in mammalian cells, Genes & Development, 2001, 15: 3237-3242.
Allen, Chris, et al., DNA-dependent protein kinase suppresses double-strand break-induced and spontaneous homologous recombination, PNAS, vol. 99, No. 6, Mar. 19, 2002, pp. 3758-3763.
Allen, Chris, et al., Interactive competition between homologous recombination and non-homologous end joining, Molecular Cancer Research, vol. 1, Oct. 2003, pp. 913-920.
Andaluz, E. et al., "Phenotypic Analysis and Virulence of *Candida albicans* LIG4 Mutants," Infection and Immunity, Jan. 2001, vol. 69, No. 01, pp. 137-147.
Ramos, W. et al., "Biochemical and genetic characterization of the DNA ligase encoded by *Saccharomyces cerevisiae* open reading frame YOR005c, a homolog of mammalian DNA ligase IV," Nucleic Acids Research 1998, vol. 26, No. 24, pp. 5676-5683.
Herrmann, G. et al., "*Saccharomyces cerevisiae* LIF1: a function involved in DNA double-strand break repair related to mammalian XRCC4," The EMBO Journal, vol. 17, No. 14, pp. 4188-4198 (1998).

* cited by examiner

Primary Examiner—Nancy Vogel
(74) Attorney, Agent, or Firm—Pearne & Gordon LLP

(57) ABSTRACT

The present invention provides a novel method of significantly promoting the ratio of homologous recombination in desirable cells. In order to enhance the ratio of homologous recombination in desirable cells such as eukaryotic cells, mutation is introduced into genes encoding factors necessary for non-homologous recombination, such as Ku70 or Ku80, or the above genes are disrupted, so as to cause the loss of the functions thereof. At the time, foreign DNA is introduced into the cells via the electroshock method or the like, so as to carry out homologous recombination, thereby promoting the frequency of homologous recombination in the cells.

9 Claims, 4 Drawing Sheets

Fig.2

| | | |
|---|---|---|
| NCKU70 | 1 | MSWRKDQDERLDGDEGDEELDENVSYHQSTHVLFAIDVSKSMLKPPQNTG |
| KU70 | 1 | MSGWESYYKTEGDEEAEEEQEENLEASGDYKYSGRDSIIFLVDASKAMFE |
| NCKU70 | 51 | DKKADKDSALTAALTCAYQIMQQRIISQPKDYVGVILEGTEKSKFRDDSG |
| KU70 | 51 | SQSEDELIPFDMSIQCIQSVYISRIISSDRDLAVVFYGTEKD------K |
| NCKU70 | 101 | NGTGYPHCYLLSDLDIPGAEDVKKLKALIED-GDDEDEIMVPSKEPVIMS |
| KU70 | 95 | NSVNEKNIYVLQELDNPGAKRILELDQFKGQQGQKRFQDMVGHGSDYSIS |
| NCKU70 | 150 | NMLECANQVETTNAANFGSRRLFLVTDNDDPHAGDKQAKSSAAVRAKDLY |
| KU70 | 145 | EVLWVCANLFSDVQFKMSHKRIMLFTNEDNPHGNDSAKASRARTKAGDLR |
| NCKU70 | 200 | DLGVVIELFPESREDKKFDLSKFYDDIIYRNPAAEAGQSESPKTSKSGDG |
| KU70 | 195 | DTGIFLDLMHPKKPGG-FDISLFYRDIIS--------IAEDEDLRVHFEE |
| NCKU70 | 250 | LTLLNSLISNLNSKQTPKRSYFSNLPFELAPGLTISIKGYMPENRQTPTR |
| KU70 | 236 | SSKLEDLERKVRAKETRKR-ALSRLKLKLNKDIVISVGIYNLVQKALKPP |
| NCKU70 | 300 | SCYVYEGEEQAQVVQSETAQVDFAVRTVEKSELRKGYKEGGEHICFKPEE |
| KU70 | 285 | PIKVYRETNEPVKTKLRTFNTSTGC-LELPSDTKRSQIVGSRQIILEKEE |
| NCKU70 | 350 | LAELKQMGKKTLRIIGFKKRSKIPSWASVAKSIELELSEEQYVGSIRVFS |
| KU70 | 334 | TEELKRFDDPGIILMGFKPLVLLKKHHYLRPSLEVMPEESLVIGSCTLFS |
| NCKU70 | 400 | ALWQKILKDEKVGLAWEVAREDNABLVMVALFPSGNPDDEEANTPYLPAGL |
| KU70 | 384 | ALLIKQDEKIVAALCRYTERRNIPLYFVALVPQEEELDDQK-IQVTPPGF |
| NCKU70 | 450 | WLYPLPFADLVRSVDHVTAPPRPADELTDQMRQVIQNLQLPKAMYDPRKY |
| KU70 | 433 | QVFLPFADKKR-KMPFTEKIMATPEQVGKMKAIVEKLRFT---VRSDSF |
| NCKU70 | 500 | PNESLQWHYKILQAKALDEETPDAMDDVTLPKYRQIDKRVGGYLAEWKEM |
| KU70 | 479 | ENEVLQQHETNLEALALDLMEPEQAVDLTLPKVEAVNKRLGSLVDEEKEI |
| NCKU70 | 550 | PAKKANDLQNTRAFKREFEEDDERPAKRAKPSKKAASGGGGPANSNADLK |
| KU70 | 529 | VYPPDYNPE-------GK------VTKRKEDNEGSGSKRPKVEYSEEELK |
| NCKU70 | 600 | KAFEQGTLGKMTVAELKDIMASKGISTAGRKAELVERLEQWVEENL |
| KU70 | 566 | THISKGTLGKFTVPMLKEACRAYGPKSGLKKQELLEALTKHFQD- |

PHR1, PHR2, PHR3, PHR4, PHR5

Fig.3

```
NCKU80    1  ---MAD EA TVYV DLGES ADCHN GRNE SDLE FGMR YLWDK TTTVAAS
KU80      1  MVRSCNKA VVLCMDVGF MSNSIPG-DESPFE QAKE VITMFVQRQVFAE
                                    PHR1

NCKU80   48  RKTWN VGV GLN TDE IN NENREEYQG YEN ISVLQEL GPMTMAS RAIKS
KU80     50  NKDE-IAV LFG TDG TDN PLSGG--DQYQNIT VHRHL MLPDFDL ED ES
                                    PHR2

NCKU80   98  KIEPSS TSSADAISA IV VALRM IQTFTKKLKY KRKI IVV NGES PIDDDQ
KU80     97  KIQ GS QQADFLDAL IV SMDV QHETIGKKFEKRH IE IFT DLSSRFSKSQ

NCKU80  148  SEEVANM NDVG IE IVLGVDFDDA YGFK EDKPRH KEQNEKILKTL VD
KU80    147  LD I IHS LKKCD I SL QFFLPFSLGK ED GSGD RGDGPFR LGGHGPSFPLKG

NCKU80  198  HCE SGAF TMAQA EE ATPRIKS RPFKA DGPL TLGDPQ KYPSALS Q
KU80    197  IT QQKE LEIVK MVM SLEGEDG DEIYS SES RKLCVF KKIERHS H

NCKU80  248  VERYFKTKRATPPSASNVANPNGPPQTQV NEDD VPFSGVGLQP KQLR
KU80    247  WPCRLTIGSNLSIRIAAYKSILQERVKKT VVD KTLK---KED QKET

NCKU80  298  T RI D SKAAGGKK DVDM EDL AKAY GRT VPFGKSEEDY KYE T- S
KU80    294  V C NDD----DET VLKED I QG RY GSDI VPFSK VDEE MKYK SEGK C

NCKU80  347  FTLLG VPM SSYEPFLN MG-ETGL VA K VN E AE GLSALIHAL HE S
KU80    340  FSVL G CKSS QVQRRFF MGNQVLKV FAA RDDE AAA VLSSLIHAIDE M

NCKU80  396  YA ARY VNKD APPQLL LK NPA EDDIE I YD P LPEAEDV SYQEP-
KU80    390  VA VR AYDK AN POVGMAF --H KHNYEC VYM LPF MED RO MESS
                                    PHR3                        PHR4

NCKU80  445  --------PLDKV T ITGN VL TEHRL LPNND LQQA SDY VDAMDI TEYGQ
KU80    438  LKNSKKYA TEAQL NAVDAL DSMS AKKD EKTDT EDL FPTTK PNPRF

NCKU80  487  D--------DDG H AE YA -----IDD YN --------V HHMNQAIRN
KU80    488  QRLFQCLLHRA HP EPL PIQQH WN LN PPAEVTTKSQ PLSKIKTLF
                                    PHR5

NCKU80  516  RA NPDAPLPPV EI TRFT PPEP LLA A TEID ---------LIQAA
KU80    538  PL EAKKKDQVTA QE FQDN EDG TAKK L EQG AHFSVSSLAEGSVT

NCKU80  557  E KKAEDD TIE AAK QMGN----------IICKLVS SFADVL PRAAE
KU80    588  S GSVNPAE NFR LVK KKASFEEASNQLINHIEQFLD TNETPY M SID

NCKU80  597  N RVM REEL NMEVPTL NK I TKLK ES LSVSESK SMGGS TGSGEDTD
KU80    638  C RAF REEA IKFSEEQR NN F KA QEKV EIKQLNH FWEIV QDGITLIT

NCKU80  647  EERQRKHPF A VG-----------------
KU80    688  K EEASGSSV AEE AKKFLAPKDKPSGDTAAVFE EGGDVDDLLDMI
```

METHOD OF CONDUCTING HOMOLOGOUS RECOMBINATION

TECHNICAL FIELD

The present invention relates to a method of efficiently conducing homologous recombination, and homologous recombinant cells obtained by the above method.

BACKGROUND ART

To date, mainly two recombination pathways, namely, a homologous recombination pathway and a non-homologous recombination pathway have been identified in eukaryotic cells. Homologous recombination is induced by the interaction between homologous sequences of DNA, whereas non-homologous recombination is irrelevant to such DNA homology and it is considered to conduct a direct ligation of cleaved double-stranded ends. In the case of budding yeast, a homologous recombination system has mainly been used as a recombination mechanism. If foreign DNA has a portion homologous to the genomic sequence of DNA, into which it is to be incorporated, at both ends thereof, the foreign DNA can be incorporated into the genomic site homologous to the sequence (Takata et al., 1997; Wach et al., 1994). It has been reported that Rad51, Rad52, and Rad54 are essential in this process (Nickoloff and Hoekstra, 1998). On the other hand, many other living bodies including humans, plants, insects, and fission yeasts have mainly used a non-homologous recombination system as a recombination function. In these living bodies, even if foreign DNA has a long DNA sequence portion that is homologous to a specific region on the genome, it is incorporated into the specific region with low frequency, and it is incorporated at random into the genome in many cases.

Homologous recombination enables efficient modification of the existing genes. Since it can be used for the production of a new species of strains or the improvement of decreased functions of cells, a large number of attempts to increase the ratio of homologous recombination have been made in eukaryotic cells other than budding yeasts, to date.

For example, an attempt to construct a high expression system of the RAD51 gene, RAD52 gene, or the homolog gene thereof, which plays an important role in the homologous recombination of budding yeasts, has been made. However, it has been known that even if such RAD51 or RAD52 is allowed to express at a high level, homologous recombination ratio is increased only by approximately 2 or 3 times, and that it rather adversely affects cells (Yanez and Porter, 2002; Reiss et al., 2000). In addition, various types of targeting vectors have been developed to increase the ratio of homologous recombination. For example, a method to concentrate homologous recombinants (please refer to patent Document 1 and Non-Patent Documents 1 and 2) based on the negative-positive selective method in mammalian cells or plant cells is a representative example. However, even if such a method is applied, homologous recombination frequency is still extremely low (1% or less). Moreover, since application of such a method requires complicated operations, this has not been a practical method.

With regard to studies about genetic recombination in eukaryotic cells other than budding yeasts, since genetic approach can easily be carried out, such studies have been conducted not only using fission yeasts but also using filamentous fungi. A type of filamentous fungi, *Neurospora crassa*, is one of organisms often used in studies regarding recombination. It has been known that the mei-3, mus-11, and mus-25 genes of *Neurospora crassa* are homologous to RAD51, RAD52, and RAD54, respectively, which function in the homologous recombination of budding yeasts. Thus, the ratio of homologous recombination of a mutant comprising a deletion regarding these genes has been studied (Handa et al., 2000) by measurement of homologous-integration frequency of the mtr gene contained in the plasmid pMTR (Schroeder et al., 1995) into the chromosomal mtr locus as an indicator. Only 3% to 5% of transformants exhibited homologous integration in wild-type strain. In contrast, in the case of mei-3 and mus-25 mutants, almost no such homologous recombination took place. These data also showed that the ratio of homologous recombination is extremely low in *Neurospora crassa*, and that it is not easy to disrupt a specific gene by gene targeting.

On the other hand, it has been reported that a non-homologous recombination process progresses via DNA-dependent protein kinase (DNA-PKcs), a K70-Ku80 heterodimer, and a DNA ligase IV-Xrcc4 complex (please refer to Non-Patent Documents 3, 4, and 5). Thus, the inventor has conducted studies based on a working hypothesis that the ratio of homologous recombination would be increased by inhibition of the non-homologous mechanism.

Patent Document 1: Japanese Patent Application Laid-Open No. 2001-046053
Non-Patent Document 1: Terada et al., Nature biotech. 20, 1030-1034. 2002
Non-Patent Document 2: Jeannotte et al., E J. Mol. Cell Biol. 11, 5578-5585. 1991
Non-Patent Document 3: Gallego et al., the Plant Journal, 35, 557-565. 2003
Non-Patent Document 4: Walker et al., Nature 412, 607-614. 2001
Non-Patent Document 5: Critchlow and Jackson, TIBS, 23, 394-398. 1998

DISCLOSURE OF THE INVENTION

Problems to be Solved by the Invention

Under the aforementioned circumstances, the present inventor has conducted intensive studies directed towards the discovery of a method of increasing the ratio of homologous recombination in eukaryotic cells. As a result, the inventor has unexpectedly found that the homologous recombination ratio in eukaryotic cells can be increased by the loss of the functions of KU70 and KU80, which are genes necessary for non-homologous recombination, or by a decrease in such functions.

Accordingly, it is an object of the present invention to provide a method of increasing the ratio of homologous recombination.

In addition, it is another object of the present invention to provide high efficient homologous recombinant cells produced by the above method.

Means for Solving the Problems

Thus, in order to increase the ratio of homologous recombination, the present invention provides a method of efficiently conducting homologous recombination, which comprises causing a decrease in the functions of genes that have been known to be necessary for non-homologous recombination or the loss of the functions thereof via means such as mutagenesis or gene disruption, and then introducing desired foreign DNA used to be conducted by homologous recombination into the genes.

The efficiency of homologous recombination realized using the method of the present invention is, for example, 70% or more, and more preferably 80%, 81%, 82%, 83%, 84%, 85%, 86%, 87%, 88%, 89%, 90%, 91%, 92%, 93%, 94%, 95%, 96%, 97%, 98%, 99% or more. Most preferably, 100% of homologous recombination frequency can be realized.

In general, cells used in the present invention may be either cells derived from tissues, or a cultured established cell line. Thus, the types of the cells used in the present invention are not limited, as long as they are eukaryotic cells. Suitable cells may include animal cells, plant cells, and fungal cells, which have a low ratio of homologous recombination.

Examples of animal cells used herein may include: mammalian cells such as those of a human, mouse, rat, bovine, swine, horse, chicken, sheep, feline, or canine; and those of Aves, reptiles, amphibians, and others.

Examples of plant cells used herein may include those of rice, soybean, wheat, barley, rye, cotton, starch, potato, peanut, and Arabidopsis.

Moreover, fungal cells wherein genetic manipulation is relatively easily carried out or other cells can also be used. The cells of filamentous fungi or the like are preferable. Examples of filamentous fungi used herein may include genus *Neurospora*, genus *Aspergillus*, genus *Penicillium*, genus *Fusarium*, genus *Trichoderma*, and genus *Mucor*. Of these, examples of preferred filamentous fungi, which are preferably used herein, may include: *Neurospora crassa*, *Neurospora sitophila*, *Neurospora tetrasperma*, and *Neurospora intermedia*, which belong to genus *Neurospora*; and *Aspergillus oryzae*, *Aspergillus sojae*, *Aspergillus niger*, *Aspergillus awamori*, *Aspergillus kawachi*, *Aspergillus parasiticus*, *Aspergillus flavus*, *Aspergillus nomius*, *Aspergillus fumigatus*, and *Aspergillus nidulans*, which belong to genus *Aspergillus*.

The types of genes necessary for non-homologous recombination used in the present invention are not limited, and those that have been known in the present technical field can be used. Preferred examples may include genes encoding DNA-dependent protein kinase (DNA-PKcs), a K70-Ku80 heterodimer, a DNA ligase IV-Xrcc4 complex, etc. In particular, the KU70 gene and/or the KU80 gene are most preferable.

Ku70 and Ku80 used in the present invention include the Ku70 and Ku80 homologs of any given eukaryotes. For example, genes including human Ku70 (P12956) (SEQ ID NO: 1), human Ku80 (P13010) (SEQ ID NO: 2), *Neurospora crassa* Ku70 (NCU08290.1) (SEQ ID NO: 3), *Neurospora crassa* Ku80 (NCU00077.1) (SEQ ID NO: 4), etc., and also genes, which encode an amino acid sequence comprising a deletion, addition, or substitution of one or several amino acids with respect to the gene products thereof, which have activity necessary for non-homologous recombination, can be used as the Ku70 and Ku80 homologs of the present invention.

The type of a method of introducing DNA into cells used in the present invention is not particularly limited. Any method can be used, as long as it has been publicly known in the present technical field. Examples of such an introduction method used herein may include the spheroplast method, the electroshock method (electroporation method), the calcium phosphate method, and a method using cationic lipids. Of these, the electroshock method (electroporation method) is most preferable.

The present invention also provides cells having a significantly increased ratio of homologous recombination, which are produced by the method of the present invention.

Advantages of the Invention

Since the present invention achieves almost 100% of homologous recombination ratio in target cells, disruption, substitution, or the like of a gene of interest can efficiently be carried out. In addition, it becomes possible to insert the gene of a heterogeneous organism into the specific genome region of target cells, so as to allow the above gene to express therein.

BRIEF DESCRIPTION OF THE DRAWINGS

FIG. 2 shows the comparison of the putative amino acid sequence of an ncKu70 protein with the putative amino acid sequence of a human Ku70 protein. The frame with a solid line indicates a Ku70/80 DNA binding domain, the frame with a broken line indicates a Ku80 binding region, and the frame with a dotted line indicates an SAP domain. In addition, the region PHR particularly conserved in Ku of various types of organisms is indicated with an underlined italic type.

FIG. 3 shows the comparison of the putative amino acid sequence of an ncKu80 protein with the putative amino acid sequence of a human Ku80 protein. The frame with a solid line indicates a Ku70/80 DNA binding domain, the frame with a broken line indicates a Ku80 binding region, and the frame with a dotted line indicates a DNA-PKcs binding domain. In addition, the region PHR particularly conserved in Ku of various types of organisms is indicated with an underlined italic type.

BEST MODE FOR CARRYING OUT THE INVENTION

Figure 1:
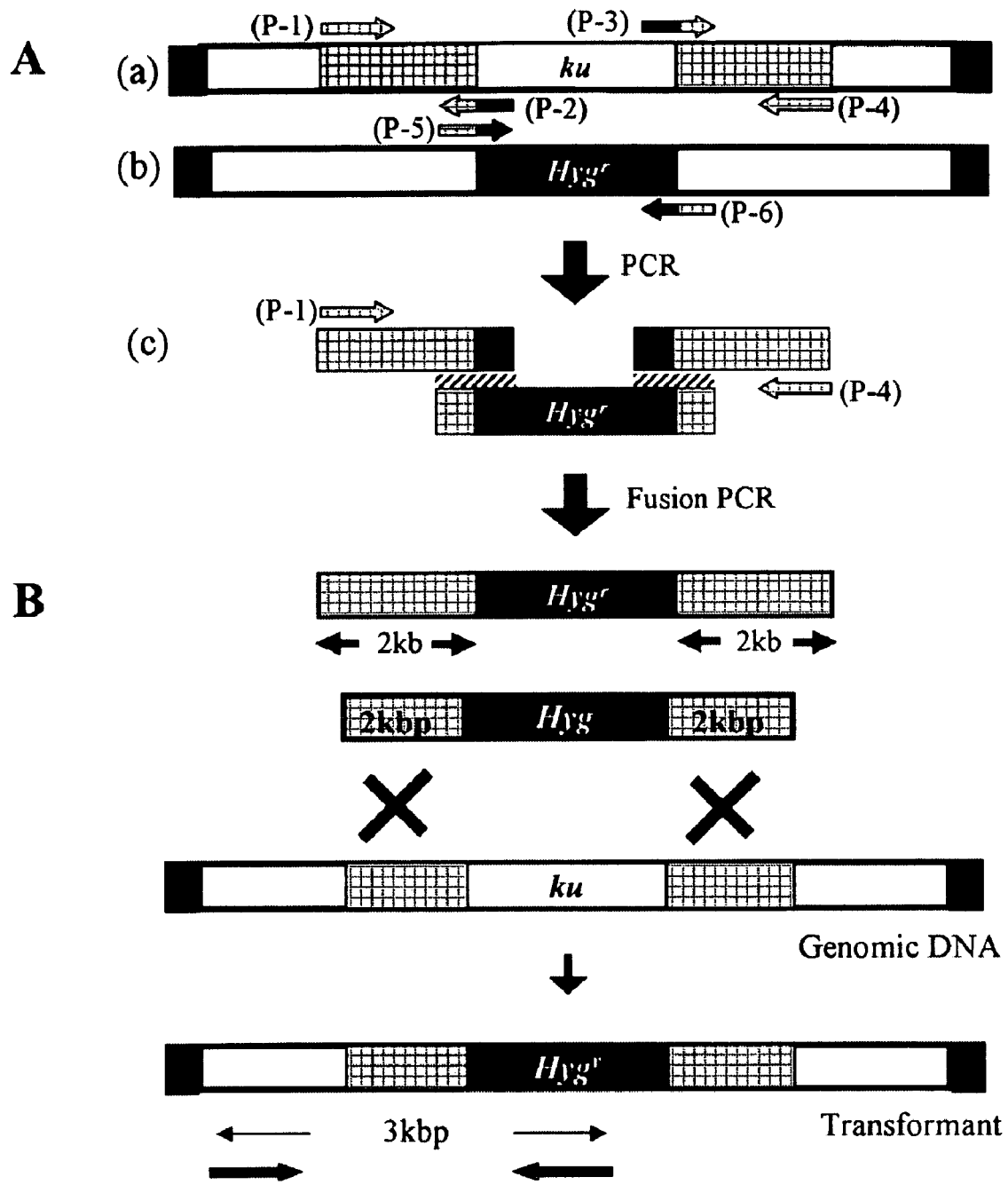
FIG. 1 shows a method of substituting ncKU70 and ncKU80 with Hyg$^r$. A indicates a method of constructing an ncKU target vector. The 5'-region of the ncKU gene was amplified with (p-1) (SEQ ID NO: 5) and (p-2) (SEQ ID NO: 6), and the 3'-region thereof was amplified with (p-3) (SEQ ID NO: 7) and (p-4) (SEQ ID NO: 8). The Hyg$^r$ gene was amplified with (p-5) (SEQ ID NO: 9) and (p-6) (SEQ ID NO: 10). B indicates homologous incorporation of a fusion PCR product into the target gene.

1. Identification of Genes Encoding Factors Necessary for Non-homologous Recombination in Target Cells In the present invention, in order to introduce a function decrease or function loss into genes encoding factors necessary for non-homologous recombination, it is necessary to identify the genes encoding factors necessary for non-homologous recombination derived from the target cells. In the case of identifying a Ku70 or Ku80 homolog, for example, when the gene sequence of such a Ku70 or Ku80 homolog derived from the target cells has been unknown, the cDNA library, etc. of the target cells is screened based other known species such as the homolog gene sequence of human Ku70 (SEQ ID NO: 1) or Ku80 (SEQ ID NO: 2). As a screening method, a method regarding nucleic acid hybridization and cloning, which has been publicly known in the technical field, is used, and the Ku70 or Ku80 homolog can be obtained by hybridization at a low, middle, or high stringent level. The "stringency" of the hybridization is easily determined by persons skilled in the art, and it is an empirical condition that depends on a probe length, a washing temperature, and a salt concentration. When hybridization screening is carried out to identify a homolog, persons skilled in the art can easily understand how to control a temperature, an ionic strength, or the like, while taking into consideration the length of a probe or the like.

Moreover, when the database of ORF derived from target cells exists, it is also possible to conduct BLAST search or the like against the above database, so as to identify a homolog of the known KU70 or KU80. In this case, it is also possible to clone KU70 or KU80 of interest by preparing suitable PCR primers used to amplify the corresponding gene as a whole based on the searched sequence, and then inserting the obtained PCR product into a suitable cloning vector.

The identified KU70 or KU80 is subcloned into a suitable cloning vector (for example, pUC19), so as to confirm its sequence.

2. Decrease or Loss of Functions of Gene Necessary for Non-homologous Recombination The present invention provides a method of increasing homologous recombination frequency on the chromosome by causing a decrease in the functions of a gene necessary for non-homologous recombination existing in cells or the loss of the functions thereof. For such a purpose, the functions of a gene necessary for non-homologous recombination existing in cells can be modified. The type of such a method of modifying the functions is not limited. Examples of a method used herein may include methods publicly known to persons skilled in the art, such as a method of introducing a mutation into a gene necessary for non-homologous recombination existing in cells, a method using RNA interference (RNAi), a method of disrupting the gene as a whole necessary for non-homologous recombination, or a method of introducing an antisense strand corresponding to a gene necessary for non-homologous recombination into cells. Preferred methods include a method of introducing a mutation into a gene necessary for non-homologous recombination existing in cells, a method using RNA interference (RNAi), and a method of disrupting the gene as a whole necessary for non-homologous recombination. More preferred methods include a method using RNA interference (RNAi) and a method of disrupting the gene as a whole necessary for non-homologous recombination. The most preferred method is a method of disrupting the gene as a whole necessary for non-homologous recombination.

As a method of disrupting the gene as a whole, there is a method of transforming cells with DNA, which has been produced by inserting a marker gene into the essential region of the cloned target gene. The DNA introduced into the cells induces homologous recombination via both sequences adjacent to the target gene, and it is able to disrupt the target gene on the chromosome via the marker gene (Alfa et al., 1993).

In addition, for the purpose of the loss of gene functions, RNA interference (RNAi) can be used. In this case, based on a nucleotide sequence associated with the function domain of a factor of interest that causes the function loss, short double-stranded RNA or a vector for generating the above RNA is introduced into cells, so as to bring on a decrease in the functions of the above factor or the loss of the functions thereof.

Moreover, as a method of introducing a mutation into cells in vitro, there are applied methods known in the present technical field, such as a site-directed mutagenesis or PCR mutagenesis. Such a site-directed mutagenesis (Carter, 1986; Zoller and Smith, 1987), a cassette mutagenesis, a target-selected mutagenesis (Wells et al., 1985), or other known techniques, are carried out on DNA, which has been prepared for introduction of a mutation into a gene of interest and has been then cloned (Ausbel et al., 1987; Sambrook, 1989).

When a mutation is introduced into KU70 or KU80, so as to modify the functions thereof, it is desired to introduce a mutation such that the Ku70 protein or Ku80 protein activity can be lost, or to introduce a mutation into a site necessary for the interaction between the Ku70 protein and the Ku80 protein, so as to delete the above interaction.

3. Measurement of Recombination Activity

The degree of homologous recombination is measured, based on the ratio of the cells transformed by recombination at a homologous sequence site, to the cells transformed with DNA introduced from the outside of the cells.

Examples will be given below. However, these examples are not intended to limit the scope of the present invention.

EXAMPLE 1

*Neurospora crassa*

1. Experimental Materials

Table 1 shows the *Neurospora* strains used in the present experiment. C1-T10-37A and C1-T10-28a were used as wild types (Tamaru and Inoue, 1989). The *Escherichia coli* DH1 and XL-1 Blue strains were used to amplify plasmids (Sambrook et al., 1989).

The plasmids pBluescript SK+ (Stratagene) and pGEM (Promega) were generally used to construct new vectors. The two plasmids pBARGEM7-1 (Pall and Brunelli, 1993) and pCSN43 (Staben et al., 1989), and the two cosmids G7H3 and G8B12 were acquired from Fungal Genetics Stock Center, University of Missouri, Kansas City, 5007 Rockhill Rd., Kansas City, Mo. 64110.

TABLE 1

Table 1. *Neurospora crassa* strains used in the present invention

| Strain | Genotype | Source/Publication |
|---|---|---|
| C1-T10-37A | A | Stock in the laboratory |
| C1-T10-28a | a | Stock in the laboratory |
| 54yo-728-5 | A ncku70 | Produced in the present experiment |
| 54yo-728-7 | a ncku70 | Produced in the present experiment |
| 54yo-828-3 | A ncku80 | Produced in the present experiment |
| 54yo-828-4 | a nku80 | Produced in the present experiment |
| FGSC#2764 | A mei-3 | FGSC* |
| FGSC#6409 | A mus-11 | FGSC* |

*FGSC: Fungal Genetics Stock Center

2. Methods (1) Genetic Research Method of *Neurospora*

The gene analysis was carried out in accordance with the descriptions of Davis and de Serres (1970).

(2) PCR Method

PCR amplification was carried out using Expand™ High-Fidelity PCR system (Roche Diagnostics Corp., Switzerland) in accordance with the instructions included therewith.

(3) Construction of Plasmid used in Substitution of KU Homolog Genes (hereinafter referred to as ncKU70 and ncKU80) of *Neurospora crassa* with Hyg Gene A method of substituting ncKU70 and ncKU80 with the hygromycin-resistance gene Hyg$^r$ is shown in FIGS. 1A and 1B.

(a) Preparation of DNA used in Substitution of ncKU70

The 5'- and 3'-flanking DNAs of the *Neurospora* KU70 gene, each having a length of 2 kbp, were amplified by PCR using the cosmid G7H3 as a template (PCR conditions: after a reaction of 94° C. and 2 minutes, a cycle consisting of 94° C. and 15 seconds, 58° C. and 30 seconds, and 72° C. and 2 minutes, was repeated 10 times, and then, a cycle consisting of 94° C. and 15 seconds, 58° C. and 15 seconds, and 72° C. and 2 minutes, was repeated 20 times (wherein the period of time for 72° C. was extended by 5 seconds for every cycle), and thereafter, a reaction of 72° C. and 7 minutes was further carried out, followed by conservation at 4° C.).

5'-flanking DNA primers:
(SEQ ID NO: 5)
(p-1) 5'-GTGCTGTAGCCGTTTTGGGTATCGC-3'

(SEQ ID NO: 6)
(p-2) 5'-GGCGTAATAGCGAAGAGATAGTTGCTGGAAATAA-3'

3'-flanking DNA primers:
(SEQ ID NO: 7)
(p-3) 5'-AAGCATAAAGTGTAAAGGCTTGTTGATGACCGT-3'

(SEQ ID NO: 8)
(p-4) 5'-TTGGACGCCGCACACCTCTCGCTCT-3'

Subsequently, PCR amplification was carried out using the Hyg gene plasmid pCSN43 as a template (wherein PCR conditions were the same as those described above).

(SEQ ID NO: 9)
(p-5) 5'-TTATTTCCAGCAACTATCTCTTCGCTATTACGCC-3'

(SEQ ID NO: 10)
(p-6) 5'-CACGGTCATCAACAAGCCTTTACACTTTATGCTT-3'

The aforementioned three PCR products were mixed, and the obtained mixture was used as a fusion PCR template (Kuwayama et al., 2002). In addition, (p-1) (SEQ ID NO: 5) and (p-4) (SEQ ID NO: 8) were used as primers, so as to carry out fusion PCR under the following conditions: a cycle consisting of 94° C. and 2 minutes, 94° C. and 15 seconds, and 60° C. and 30 seconds, was repeated 10 times, and then, a cycle consisting of 94° C. and 15 seconds, 60° C. and 30 seconds, and 68° C. and 5 minutes, was repeated 20 times (wherein the period of time for 68° C. was extended by 1 minute for every cycle), and thereafter, a reaction was carried out at 72° C. for 7 minutes, followed by retention at 4° C.). The obtained fusion PCR product was electrophoresed on 0.7% agarose gel, and wild-type Neurospora was then transformed with it.

(b) Preparation of DNA used in Substitution of ncKU80

The 5'- and 3'-flanking DNAs of the *Neurospora* KU80 gene, each having a length of 2 kbp, were amplified by PCR using the cosmid G8B12 as a template (wherein PCR conditions were the same as those for ncKU70).

5'-flanking DNA primers:
(SEQ ID NO: 11)
(p-7) 5'-GCGCCGGGAGGTTGTTCGTAAGCTG-3'

(SEQ ID NO: 12)
(p-8) 5'-GGCGTAATAGCGAAGAGGCTTTTCGGCTTTGCTG-3'

3'-flanking DNA primers:
(SEQ ID NO: 13)
(p-9) 5'-AAGCATAAAGTGTAAAGCAGGGTTGGAGACAGGT-3'

(SEQ ID NO: 14)
(p-10) 5'-AAGGCGGAGTTGTTGGCTGCGAAGG-3'

Subsequently, PCR amplification was carried out using the Hyg$^r$ gene plasmid pCSN43 as a template (wherein PCR conditions were the same as those for ncKU70).

(SEQ ID NO: 15)
(p-11) 5'-CAGCAAAGCCGAAAAGCCTCTTCGCTATTACGCC-3'

(SEQ ID NO: 16)
(p-12) 5'-ACCTGTCTCCAACCCTGCTTTACACTTTATGCTT-3'

Fusion PCR was carried out using (p-7) (SEQ ID NO: 11) and (p-10) (SEQ ID NO: 14) under the aforementioned conditions.

(4) Electroshock Method (Electroporation Method)

A conidiospore suspension was prepared at a concentration of $2.0 \times 10^9$ in 1 M sorbitol. 30 μl of the fusion PCR product was mixed with 50 μl of the conidiospore suspension, and the mixture was then incubated on ice for 5 minutes. Thereafter, 40 μl of the mixed solution was added to cells on an electroporator (BTX Electro Cell Manipulation 600 Genetronics Inc.). The following conditions were applied to the electroshock: charged voltage: 1.5 kV; peak in the voltage/time mode: 2.5 kV/resistance; time capacitance: 50 μF; and time resistance: R6 (186 ohms).

(5) Substitution of ncKU70 and ncKU80

After completion of the electroshock, 1 ml of Vogel's minimal medium that contained 1.2% sucrose was added to the resultant, and the obtained mixture was then incubated at 30° C. for 2 hours. 200 μl of the obtained solution was applied to and expanded on an agar medium that contained hygromycin B (500 μg/ml). A hygromycin-resistance colony was isolated, and it was then confirmed by PCR whether or not substitution took place in the target locus. In addition, it was also confirmed by the Southern blot method whether or not it contained redundant Hyg$^r$ gene copies.

(6) Mutagene Sensitivity

Sensitivity to UV and methyl methanesulfonate (MMS) was examined according to the method described in the already issued publication (Inoue and Ishii, 1984).

3. Results (1) Substitution Experiment of ncKU70 and ncKU80

Figure 4:
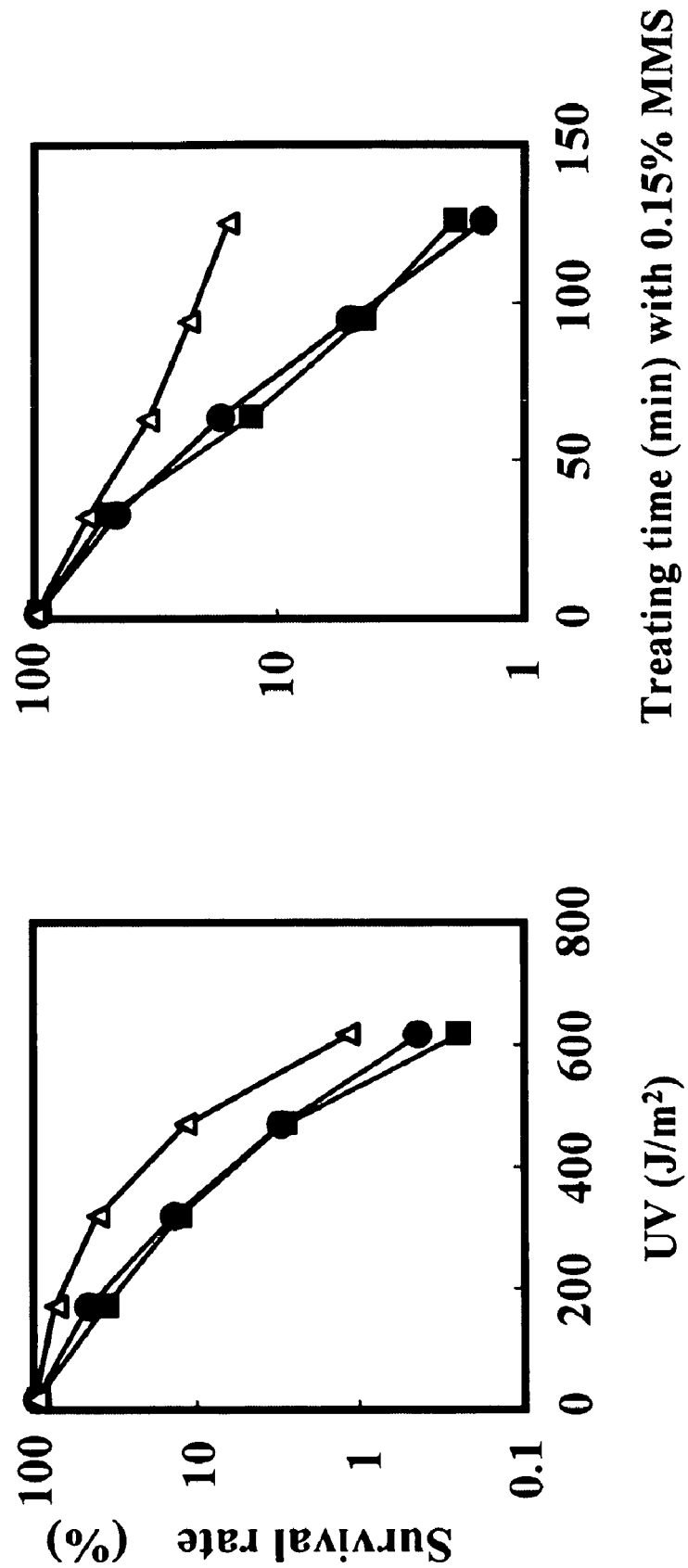
FIG. 4 shows The UV and MMS sensitivity of a wild-type strain, the ncKu70, and ncKu80 strains. The open triangle indicates the wild-type strain, the filled circle indicates ncKu70, and the filled square indicates ncKu80. The experiment was carried out at least 3 times. Each point indicates the mean value of data.

In order to discover a homolog of *Neurospora crassa* to human KU70 and KU80, search was conducted against *Neurospora* genome database (http ://www-genome.wi.mit.edu/annotation/fungi/*neurospora*). The retrieved candidate genes were temporarily named as ncKU70 and ncKU80. The ncKU70 and ncKU80 genes encode 645 and 661 amino acids, respectively. FIG. 2 shows the comparison of the amino acid sequence of human Ku70 with the amino acid sequence of ncKu70. Human Ku70 and ncKU70 had an identity of 23% and a similarity of 42%. FIG. 3 shows the comparison of human Ku80 with ncKU80. Human Ku80 and ncKU80 had an identity of 23% and a similarity of 41%. G7H3 and G8B12 obtained from the Orbach/Sachs cosmid library (Orbach, 1994) contained ncKU70 and ncKU80, respectively. Accordingly, using these cosmids as templates, ncKU70 and ncKU80 were amplified by PCR. As described in the sections regarding materials and methods, a DNA fragment retaining a Hyg$^r$ gene, to which 5'- and 3'-flanking DNAs with a length of 2 kbp derived from the ncku gene bound, was prepared by fusion PCR. The fusion PCR product was introduced into wild-type *Neurospora crassa*, and a hygromycin-resistance colony was then isolated. Approximately 200 transformants were subcloned, and genomic DNA was then extracted. Thereafter, it was confirmed by PCR whether or not the ncKU gene was substituted with the Hyg$^r$ gene. As shown in FIG. 1B, one of the PCR primers was designed outside of the ncKU gene, and the other PCR primer was designed inside of the Hyg$^r$ gene. Approximately 10% of hygromycin-resistance colonies had the Hyg$^r$ gene at the position of the ncKU gene. ncKU70 (the 54yo-728 strain retaining Hyg$^r$) and ncKU80 (the 54yo-828 strain retaining Hyg$^r$) were used as ncKU70 and ncKU80 mutants, respectively. These strains were normal in terms of vegetative growth and homozygous cross proliferation. However, the strains were sensitive to UV to a small extent, and were clearly sensitive to MMS (FIG. 4).

(2) Targeting of mtr Gene and ad-3A Gene in Wild-type Strain, ncKU70, ncKU80, mei-3, and mus-11 Mutant Strains The mtr gene and ad-3A gene on the chromosomes IV and I were selected as targets of a substitution experiment. A mutant having a deletion in the mtr gene shows resistant to p-fluorophenylalanine (PFP), which is an amino acid analog. A mutant having a deletion in the ad-3A gene shows accumulation of purple pigments (please refer to the *Neurospora Compendium*, Academic Press, 2001). The mtr ORF or ad-3A ORF was substituted with the blasticidin-resistance gene bar, so as to construct a targeting vector. 2.7-kb DNA that contained the bar gene was cleaved from pBARG EM7-1 using restriction enzymes ScaI and SmaI.

(2)-1

In the case of the mtr gene, construction and introduction of a targeting vector were carried out as follows. pMTR that contained the mtr gene was digested with MscI, and an approximately 1-kbp portion that contained an mtr gene promoter and a portion of ORF was eliminated. Subsequently, a 2.7-kbp bar fragment was inserted into the above portion, so as to produce the plasmid pGS1 (9.5 kbp). The plasmid pGS1 was digested with NotI. Thereafter, the thus obtained 6.7-kbp linear fragment that retained 1.8-kbp 5'- and 1.9-kbp 3'-flanking DNAs of the mtr gene at both ends of the bar gene was introduced into a strain having different genetic background by the electroporation method. Transformants that were resistant to blasticidin (200 µg/ml) were isolated, and it was then examined whether or not such transformants were resistant to PFP (20 µg/ml). If the bar-DNA had been changed for the mtr locus, it should have shown resistance to PFP. Thus, it was further examined whether or not recombination was carried out by homologous substitution. Table 2 shows that 10% to 30% of blasticidin-resistance transformants were generated as a result of homologous recombination in wild-type strains. In contrast, al the transformants of the ncKU70 and ncKU80 strains were generated as a result of homologous recombination. In the case of the mei-3 and mus-11 strains having a deletion in homologous recombination repair, almost no such homologous recombination took place.

TABLE 2

| Strain | Experiment No. | Bla-resistance | PFP-resistance | Homologous recombination frequency (%) |
|---|---|---|---|---|
| Wild type | 1 | 9 | 3 | |
| | 2 | 22 | 3 | |
| | 3 | 11 | 3 | |
| | 4 | 16 | 2 | |
| | Total number | 58 | 11 | 19 |
| ncku70 | 1 | 41 | 41 | |
| | 2 | 18 | 18 | |
| | Total number | 59 | 59 | 100 |
| ncku80 | 1 | 12 | 12 | |
| | 2 | 23 | 23 | |
| | 3 | 12 | 12 | |
| | 4 | 26 | 26 | |
| | Total number | 73 | 73 | 100 |
| mei-3 | 1 | 58 | 2 | |
| | 2 | 35 | 1 | |
| | Total number | 93 | 3 | 3* |
| mus-11 | 1 | 45 | 0 | |
| | 2 | 20 | 0 | |
| | Total number | 65 | 0 | 0 |

(2)-2

An ad-3A targeting vector that retained 1.6-kbp 5'- and 2-kbp 3'-flanking DNAs of ad-3A at both sides was constructed in the same manner as in the case of the aforementioned mtr gene. The above vector was introduced into various types of strains. Blasticidin-resistance transformants were isolated, and sub-culture was then carried out in a minimal medium, to which adenine had been added, for 10 days. Thereafter, the number of colonies of purple mycelia, which indicate the loss of the functions of ad-3A, was counted. As shown in Table 3, approximately 50% of wild-type blasticidin-resistance transformants were purple mycelia. In contrast, 100% of the ncKU70 and ncKU80 transformants showed purple color. It was confirmed by PCR that these transformants were strains, which had been disrupted by homologous substitution (Table 3).

TABLE 3

| Strain | Bla-resistance | Adenine requirement | Homologous recombination frequency (%) |
|---|---|---|---|
| Wild type | 86 | 44 | 51 |
| ncku70 | 46 | 46 | 100 |
| ncku80 | 36 | 36 | 100 |

4. Relationship Between Targeting Ratio and Length of Homologous Sequence

In order to examine the relationship between the targeting ratio and the length of a homologous sequence, 50-, 100-, 500-, and 1000-bps fragments, which were homologous to the 5'- and 3'-flanking DNAs of the mtr gene, were amplified by PCR, and they were then allowed to bind to both sides of the bar gene. It was examined whether or not the blasticidin-resistance transformant was resistant to PFP (Table 4). The blasticidin-resistance transformants, into which 50-bp and 100-bp homologous DNAs had been introduced, showed almost no PFP resistance in ncKU70, ncKU80, and a wild-type strain. In the case of homology of 500-bp DNA, less than 10% of the blasticidin-resistance transformants showed PFP-resistance in the wild-type strain. In contrast, 90% or more of the blasticidin-resistance transformants showed PFP-resistance in the ncKU70 and ncKU80 strains. In the case of homology of 1000-bp DNA, less than 20% of the blasticidin-resistance transformants showed PFP-resistance in the wild-type strain. In contrast, all the blasticidin-resistance transformants showed PFP-resistance in the ncKU70 and ncKU80 strains. Accordingly, if the homologous portion has a length of at least 1000 bp, the target gene can be completely substituted.

TABLE 4

| Strain | Length of homologous sequence | Experiment No. | Bla-resistance | PFP-resistance | Homologous recombination frequency (%) |
|---|---|---|---|---|---|
| Wild type | 50 bp | 1 | 22 | 0 | |
| | | 2 | 29 | 1 | |
| | | Total number | 51 | 1 | 2 |
| ncku70 | 50 bp | 1 | 30 | 0 | |
| | | 2 | 29 | 1 | |
| | | Total number | 59 | 1 | 2 |
| ncku80 | 50 bp | 1 | 29 | 0 | |
| | | 2 | 30 | 0 | |
| | | Total number | 59 | 0 | 0 |
| Wild type | 100 bp | 1 | 20 | 0 | |
| | | 2 | 30 | 1 | |
| | | Total number | 50 | 1 | 2 |
| ncku70 | 100 bp | 1 | 8 | 2 | |
| | | 2 | 13 | 0 | |
| | | Total number | 21 | 2 | 10 |
| ncku80 | 100 bp | 1 | 14 | 0 | |
| | | 2 | 32 | 2 | |
| | | Total number | 46 | 2 | 4 |
| Wild type | 500 bp | 1 | 40 | 4 | |
| | | 2 | 40 | 3 | |
| | | Total number | 80 | 7 | 9 |
| ncku70 | 500 bp | 1 | 40 | 35 | |
| | | 2 | 39 | 37 | |
| | | Total number | 79 | 72 | 91 |
| ncku80 | 500 bp | 1 | 30 | 28 | |
| | | 2 | 39 | 36 | |
| | | Total number | 69 | 64 | 93 |
| Wild type | 1,000 bp | 1 | 9 | 3 | |
| | | 2 | 22 | 7 | |
| | | 3 | 40 | 6 | |
| | | 4 | 40 | 7 | |
| | | Total number | 111 | 23 | 21 |
| ncku70 | 1,000 bp | 1 | 4 | 4 | |
| | | 2 | 8 | 8 | |
| | | 3 | 10 | 10 | |
| | | 4 | 8 | 8 | |
| | | Total number | 30 | 30 | 100 |
| ncku80 | 1,000 bp | 1 | 31 | 31 | |
| | | 2 | 19 | 19 | |
| | | Total number | 50 | 50 | 100 |

EXAMPLE 2

*Aspergillus*

1. Cloning of KU70 Gene of *Aspergillus nidulans*

Using BLAST network service, clone information having high homology to the KU70 gene of *Neurospora crassa* was searched against genome database of *Aspergillus nidulans* (http://www-genome.wi.mit.edu/annotation/fungi/*aspergillus*/index.html). As a result, it was considered that Contig 1.132 contained the full-length KU70 gene of *Aspergillus nidulans*. The putative Ku protein of *Aspergillus nidulans* showed homology of approximately 50% to the Ku70 protein of *Neurospora crassa*. Using the genomic DNA of the *A. nidulans* FGCS A89 strain as a template, a 4045-bp fragment that contained the full-length KU70 gene was amplified by PCR with the following primers.

```
KU70/For
5'-GAGAACTGATCATGCGATGCGTGGC-3'    (SEQ ID NO: 17)

KU70/Rev
5'-CATTCGCTTGATCGACATGGTTGGC-3'    (SEQ ID NO: 18)
```

| | |
|---|---|
| Genomic DNA | 1 (50 ng) |
| Primer Forward | 1 (100 pmol) |
| Primer Reverse | 1 (100 pmol) |
| 10 × reaction buffer | 5 |
| dNTP mixture | 4 |
| Ex Taq | 1 |
| DDW (distilled water) | 37 |
| Total amount | 50 μl |

The above reaction system was prepared, and the PCR reaction was then carried out using TaKaRa PCR Thermal Cycler PERSONAL (Takara Shuzo Co., Ltd.). The reaction conditions consisted of: 1 cycle of 96° C. and 2 minutes; and 30 cycles of 96° C. and 30 seconds, 58° C. and 30 seconds, and 72° C. and 7 minutes. After completion of the PCR reaction, the reaction product was subjected to agarose gel electrophoresis, so as to recover a fragment of interest from the gel. The obtained fragment was ligated to the pGEM-T Easy vector (Promega) by the TA cloning method, so as to obtain pGEMku70.

2. Disruption of KU70 Gene of *Aspergillus nidulans* —oliC31—

Using pGEMku70 as a template, the HindIII site was introduced by the QuikChange site-directed mutagenesis method with the following primers. The underlined portions indicate HindIII sites.

```
KU70/(HindIII)/For
                                   (SEQ ID NO: 19)
5'-CACATTGTCCAAGCTTACTGTGGCTACCC-3'

KU70/(HindIII)/Rev
                                   (SEQ ID NO: 20)
5'-GGGTAGCCACAGTAAGCTTGGACAATGTG-3'
```

| | |
|---|---|
| pGEMku70 | 2 (20 ng) |
| Primer Forward | 2 (200 ng) |
| Primer Reverse | 2 (200 ng) |
| 10 × reaction buffer | 5 |
| dNTP mixture | 4 |
| Pfu Turbo | 1 |
| DDW (distilled water) | 34 |
| Total amount | 50 μl |

TaKaRa PCR Thermal Cycler PERSONAL was used for the PCR reaction. The reaction conditions consisted of: 1 cycle of 95° C. and 2 minutes; and 18 cycles of 95° C. and 30 seconds, 54° C. and 30 seconds, and 70° C. and 15 minutes. The obtained mutant plasmid was named as pGEMku70(H), and this plasmid was then digested with B1nI and HindIII. Thereafter, a fragment obtained by digesting the *Aspergillus nidulans*-derived oligomycin-resistance gene oliC31 with B1nI and HindIII was inserted therein, so as to obtain pGEMku70::oliC31. This plasmid was digested with ApaI, so as to convert it to a linear form, and it was then introduced into the *A. nidulans* FGSC A89 strain by the protoplast PEG method. Transformants were selected in a potato dextrose medium that contained oligomycin (3 μg/ml). The obtained transformants were subjected to PCR and the Southern blot analysis, so as to select KU70 gene-disrupted strains.

3. Disruption of KU70 Gene of *Aspergillus nidulans* —ptrA—

Using pGEMku70 as a template, the HindIII site was introduced by the QuikChange site-directed mutagenesis method with the following primers. The underlined portions indicate HindIII sites.

```
KU70/(HindIII)/For
                                        (SEQ ID NO: 21)
5'-CACATTGTCCAAGCTTACTGTGGCTACCC-3'

KU70/(HindIII)/Rev
                                        (SEQ ID NO: 22)
5'-GGGTAGCCACAGTAAGCTTGGACAATGTG-3'
```

| pGEMku70 | 2 (20 ng) |
| Primer Forward | 2 (200 ng) |
| Primer Reverse | 2 (200 ng) |
| 10 × reaction buffer | 5 |
| dNTP mixture | 4 |
| Pfu Turbo | 1 |
| DDW (distilled water) | 34 |
| Total amount | 50 μl |

TaKaRa PCR Thermal Cycler PERSONAL was used for the PCR reaction. The reaction conditions consisted of: 1 cycle of 95° C. and 2 minutes; and 18 cycles of 95° C. and 30 seconds, 54° C. and 30 seconds, and 70° C. and 15 minutes. The obtained mutant plasmid was named as pGEMku70(H), and this plasmid was then digested with B1nI and HindIII. Thereafter, a fragment obtained by digesting the *Aspergillus oryzae*-derived pyrithiamin-resistance gene ptrA with B1nI and HindIII was inserted therein, so as to obtain pGEMku70::ptrA. This plasmid was digested with SpeI, so as to convert it to a linear form, and it was then introduced into the *A. nidulans* FGSC A89 strain by the protoplast PEG method. Transformants were selected in a Czapek-Dox medium that contained pyrithiamin (100 μg/ml). The obtained transformants were subjected to PCR and the Southern blot analysis, so as to select KU70 gene-disrupted strains.

4. Disruption Efficiency of Any Given Gene —kexB—

In order to examine the gene disruption efficiency using a wild-type strain or Ku70-disrupted strain as a host, the efficiency was obtained by kexB gene disruption. It was clear that the kexB gene encodes processing protease KexB, and that the kexB gene-disrupted strain forms a more compact colony than a wild-type strain does. Thus, a kexB gene disruption plasmid was introduced into a wild-type stain and a Ku70-disrupted strain, and the ratio of the obtained transformants that showed the phenotype of a kexB gene disrupted strain was then examined. The results are shown below.

kexB gene disruption efficiency

Wild-type strain (FGSC A89) hosts 6/83 transformants (7.2%)

Ku70 gene disrupted stain hosts 90/100 transformants (90%)

Hence, it was succeeded that the kexB gene was disrupted at an extremely high efficiency, and it was shown that the KU70 gene-disrupted strain is a strain significantly useful for genetic analysis such as gene disruption.

EXAMPLE 3

*Arabidopsis*

1. Experimental Materials

Table 5 shows the Arabidopsis strains used in the present experiment.

Any type of target gene may be used. In this experiment, AG (At4G18960) and LFY (At5g61850) were used as target genes. As a transformation marker, the GFP gene derived from the plasmid CaMV35S-sGFP(S65T)-NOS3' was used. The GFP gene was cut out of the plasmid using HindIII and EcoRI. Thereafter, it was blunt-ended and was then inserted into the EcoRV site of pBluescript SK+ (pSKGFP). An approximately 2-kb portion located upstream of the read codon of the AG gene was amplified with a primer, to which a restriction site had been added, and it was then inserted into the site upstream of GFP of pSKGFP. Likewise, an approximately 2-bp portion located downstream of the read codon of the AG gene was inserted into the site downstream of GFP. The thus obtained portion ranging from pSKAG::GFP to AG::GFP was cut out, and it was then used for transformation. The same above operations were performed also on the LFY gene.

TABLE 5

| Disrupted gene | GenBank registration No. | Name of stock strain | Nottingham stock No. | Homolog name |
|---|---|---|---|---|
| At1g16970 | BH750130 | SALK 037071 | N537071 | K70-1 |
|  | BZ378077 | SALK 106654 | N606654 | K70-2 |
|  | BZ292117 | SALK 123114 | N623114 | K70-6 |
|  | BH750124 | SALK 037064 | N537064 | K70-3 |
| At1g48050 | BH814153 | SALK 065823 | N565823 | K80-1 |
|  | BZ762137 | SALK 089730 | N589730 | K80-2 |
|  | BH814138 | SALK 065799 | N565799 | K80-4 |
|  | BH254483 | SALK 016627 | N516627 | K80-3 |
| At5g57160 | BH864398 | SALK 095962 | N595962 | L4-1 |
|  | BH754746 | SALK 044027 | N544027 | L4-2 |

2. Confirmation of Gene Homo-disrupted Strain (1) The seeds of each strain were sterilized with 5% hypochlorous acid, and they were then inoculated in an agar medium, to which Hyponex and sucrose had been added.

(2) 10 days later, a piece of cotyledon was cut out, and DNA was then separated using Microsmash manufactured by TOMY SEIKO Co., Ltd. Using the DNA as a template, PCR was carried out with primers suitable for genomic DNA consisting of 500 bases before and after a T-DNA insertion site. Individuals, wherein amplification of genomic DNA had not been observed, were temporarily defined as gene disruption homo individuals, and they were then used in the subsequent experiment.

3. Maintenance of KU and Lig4 Disrupted Strain

Individuals, which had been confirmed to be homo-disrupted strains, were cultivated according to common methods, so as to maintain the strains.

4. Establishment of Cell Culture System and Transformation (1) Hypocotyls and leaves were cut out of young plants (which were sterilized plants allowed to grow by the aforementioned method), 2 weeks after the inoculation, and they were then sectioned at a width of approximately 1 mm.

(2) The obtained sections were placed in a callus induction medium (CIM medium produced by adding MES, sugar, a fixation agent, and plant hormone, to a B5 medium).

(3) After the callus had sufficiently grown, it was transferred to a liquid medium (MS medium produced by adding sugar and plant hormone to an MS basal medium), and it was then subjected to a shake culture.

(4) It was replanted every 1 week.

(5) A small callus was directly used in transformation (when the size of a callus was great, it was converted to a protoplast, and the means described in 5. later was applied).

(6) Calluses were collected by centrifugation, and they were then suspended in an EP buffer (70 mM KCL, 0.3 M mannitol, 5 mM 2-morpholinoethanesulfonic acid, pH 5.8). The concentration of the suspension was controlled to $1.5 \times 10^6$/ml. 800 μl of the suspension was placed in an electroporation cuvette (4 mm gap). Using ECM 600 manufactured by BTX, electroporation was carried out under conditions consisting of mode: LV; capacitance: 125 μF; resistance: 0; charged voltage: 300 volts; field strength: 750 V/cm; and pulse length: 22-26 msec. 10 μg of DNA was used in a single electroporation. (7) After completion of the electroporation, the resultant was suspended in 5 ml of a liquid medium, to which 0.5 M mannitol had been added, and the mixture was left at rest for 1 hour.

(8) Agar was added to the liquid medium, and the obtained mixture was inoculated in a consolidated Petri dish medium.

5. Production of Protoplast and Transformation (1) Hypocotyls and leaves were cut out of young plants (which were sterilized plants allowed to grow by the aforementioned method), 2 weeks after the inoculation, and they were then sectioned at a width of approximately 1 mm.

(2) The obtained sections were immersed in a 0.5 M mannitol solution for 1 hour, and they were then treated with an enzyme solution (1% cellulose Onozuka RS, 0.25% macerozyme R-10, 0.5 M mannitol, 8 mM calcium chloride, pH 5.5) for 5 to 10 hours. Thereafter, they were washed with 0.5 M mannitol 3 times.

(3) The number of cells was controlled to $2 \times 10^6$/ml, and 400 μl of the solution was placed in an electroporation cuvette (2 mm gap). DNA to be introduced was added thereto, resulting in a concentration of 5 to 10 μg/ml. Using ECM 600 manufactured by BTX, electroporation was carried out under conditions consisting of mode: LV; capacitance: 500 μF; resistance: R3 (48 ohms); charged voltage: 106 volts; field strength: 530 V/cm; and pulse length: 22-26 msec.

(4) After completion of the electroporation, the resultant was suspended in 3 ml of a modified 8p medium, and the mixture was left at rest for 1 hour.

(5) The modified 8 p medium was expanded on a medium consolidated with agarose, followed by culture.

6. Confirmation of Transformant (1) Ultraviolet ray was applied to callus that had grown after the transformation experiment.

(2) Each cell mass, wherein GFP expression had been confirmed, was replanted.

(3) After the cell mass had grown to a size of 5 mm, it was divided into two portions. One portion was transferred to a redifferentiation medium (RIM produced by adding MES, sugar, and plant hormone, to a B5 medium), and DNA was separated from the other portion. The DNA separation method was the same as that in Example 1. Using the obtained DNA as a template, PCR was carried out with primers that had been designed in the GFP gene and at a target gene site. The cell mass, wherein a fragment of a predicted size had appeared, was defined as that whose gene had been disrupted.

7. Transformation Using *Agrobacterium*

(1) The Ti vector pBI221H was treated with restriction enzymes, and a 35S promoter/GUS structural gene/NOS terminator portion was cut out.

(2) The aforementioned transformation DNA was inserted into the cut portion, and it was then introduced into Agrobacterium by electroporation. Agrobacterium, which was resistant to ampicillin and had a plasmid of interest, was selected.

(3) Agrobacterium having the transformation DNA was cultured at 28° C. overnight, and it was then suspended in an immersion suspension medium, resulting in OD600 of 0.8.

(4) In the case of using a plant body, a pot was turned bottom up, and the flower bud portion was immersed therein for 15 minutes. Thereafter, the plant was cultured for about 1 month, and seeds were then collected. Thereafter, the collected seeds were allowed to be germinated, and those, wherein light emission due to GFP had been observed, were subjected to PCR.

(5) In the case of using callus, it was immersed in a cell suspension for 2 or 3 minutes, and it was then cultured in a coexisting culture medium (N6CO medium) for 3 days. Thereafter, the culture was sterilized with carbenicillin, and the presence or absence of GFP light emission was then examined. Only the light emission portion was cultured in an MS medium containing plant hormone for 1 month. Thereafter, light emission was confirmed again, and DNA was then separated, followed by confirmation by PCR.

8. Other Transformation Experiments

The linearized transformation DNA was also used in transformation with a particle gun and in cell fusion transformation using a protoplast.

EXAMPLE 4

Concerning Disruption of Human KU70 Gene

1. Obtainment of Human KU70 Gene Information

Information regarding the nucleotide sequence of a human KU70 (G22P1) gene, exon, intron, or the like, was obtained from human genome database of Ensembl project (http://www.ensembl.org/) (http ://www.ensembl.org/Homo_sapiens/geneview?gene=ENSG00000100419).

2. Determination of Repetitive Sequence Position

The obtained nucleotide sequence information was sent to REPEATMASKER WEB SERVER (http://ftp.genome.washington.edu/cgi-bin/RepeatMasker), so as to search for a repetitive sequence, thereby determining the position of such a repetitive sequence existing in the KU70 gene.

3. Design of Primers Used for Targeting Vector

Based on the nucleotide sequence information obtained in 1 and 2 above, PCR primers used to produce homology arms, which were used for targeting vectors, were designed. Primer sequences are shown below (underlined portions indicate restriction sites used in subcloning).

(1) Case of Construction of Poly A Selection Method Vector

```
Primer pair used for 5'-side homology arm
Ku70 P2 AscI
                                       (SEQ ID NO: 23)
5'-GCTATAGGCGCGCCTCTGCATTTAAGGAGAGAATAGCTGTG-3'

Ku70 P3 NotI
                                       (SEQ ID NO: 24)
5'-AGAACAGCGGCCGCAAGAGATCTCGATCACTGCTTATGATC-3'

Primer pair used for 3'-side homology arm
Ku70 P4 NotI
                                       (SEQ ID NO: 25)
5'-CTTTAGGCGGCCGCAATTCAAGATGAGTCATAAGAGGATC-3'

Ku70 P5 SalI
                                       (SEQ ID NO: 26)
5'-CATGTCGACATTTCAAGACAGGTGAAGAGGTGACAAG-3'
```

(2) Case of Construction of Promoterless Method Vector

```
Primer pair used for 5'-side homology arm
Ku70 P2 SalI
                                       (SEQ ID NO: 27)
5'-GCTATAGTCGACTCTGCATTTAAGGAGAGAATAGCTGTG-3'

Ku70 P3 NotI
                                       (SEQ ID NO: 28)
5'-AGAACAGCGGCCGCAAGAGATCTCGATCACTGCTTATGATC-3'

Primer pair used for 3'-side homology arm
Ku70 P4 NotI
                                       (SEQ ID NO: 29)
5'-CTTTAGGCGGCCGCAATTCAAGATGAGTCATAAGAGGATC-3'

Ku70 P5 SalI
                                       (SEQ ID NO: 30)
5'-ATCGCAGGCGCGCCAGACAGGTGAAGAGGTGACAAGATAC-3'
```

4. Synthesis of Homology Arm by PCR Method (1) Materials and Devices Used

Human colon cancer-derived HCT116 genomic DNA (500 ng/µl)

KOD-Plus (thermal tolerance DNA polymerase manufactured by Toyobo)

PCR thermal cycler (TaKaRa Thermal Cycler MP, Model No. TP-3000, manufactured by Takara Shuzo Co., Ltd.)

Primer Mix, wherein each primer pair was prepared to a concentration of 10 pmol (please refer to 3 above)

| Composition of PCR reaction solution: | |
|---|---|
| HCT116 genomic DNA (500 ng/µl) | 1 µl |
| 10 × PCR buffer for KOD-Plus | 5 µl |
| 2 mM dNTPs | 5 µl |
| 25 mM MgSO4 | 2 µl |
| Primer mix (10 pmol each) | 1.5 µl |
| DMSO | 2.5 µl |
| KOD-Plus-DNA polymerase | 1 µl |
| Sterilized water | 32 µl |
| Total amount | 50 µl |

A PCR reaction was carried out with the aforementioned reaction system, using a PCR cycle cycler.

The reaction conditions consisted of: 1 cycle of 94° C. and 2 minutes; and 30 cycles of 94° C. and 15 seconds, 60° C. and 30 seconds, and 68° C. and 5 minutes.

After completion of the reaction, a DNA fragment as a PCR product was purified, and it was then digested with restriction enzymes at restriction sites added to each primer.

(2) Case of Construction of Poly A Selection Method Vector

The PCR product DNA fragment of the 5'-side homology arm primer pair (Ku70 P2 AscI/Ku 70 P3 NotI) was digested with both reaction enzymes, AscI and NotI. This DNA fragment was named as KU70 F2.

The PCR product DNA fragment of the 3'-side homology arm primer pair (Ku70 P4 NotI/Ku 70 P5 SalI) was digested with both reaction enzymes, SalI and NotI. This DNA fragment was named as Ku70 F3.

(3) Case of Construction of Promoterless Method Vector

The PCR product DNA fragment of the 5'-side homology arm primer pair (KU70 P2 SalI/Ku 70 P3 NotI) was digested with both reaction enzymes, SalI and NotI. This DNA fragment was named as Ku70 F2B.

The PCR product DNA fragment of the 3'-side homology arm primer pair (KU70 P4 NotI/Ku 70 P5 AscI) was digested with both reaction enzymes, NotI and AscI. This DNA fragment was named as KU70 F3B.

Each DNA fragment was subcloned into a pBC subcloning vector, and both ends of the DNA fragment were sequenced, so as to confirm that it was a DNA fragment containing the KU70 gene.

5. Construction of Targeting Vector Plasmid (1) Case of Construction of Poly A Selection Method Vector The DNA fragment was inserted into cloning site-modified pMC1DT-3 in the order of Ku70 F2, a puromycin-resistance gene with a promoter, and Ku70 F3, thereby constructing a poly A selection vector. The plasmid was named as pPAS-Ku70 Puro.

(2) Case of Construction of Promoterless Method Vector Plasmid

The DNA fragment was inserted into cloning site-modified pMC1DT-ApA in the order of Ku70 F2B, a poly A signal-added neomycin-resistance gene without a promoter, and Ku70 F3B, thereby constructing a poly A selection vector. The plasmid was named as pBDTA-Ku70 neo.

Both targeting vector plasmids were digested with restriction enzyme AscI, so as to linearize plasmid DNA.

6. Selection of KU70 Gene-disrupted Cells (1) Gene Disruption with Poly A Selection Method Vector The linearized pPAS-Ku70 Puro DNA produced in 5 above was introduced into HCT116 ells by the electroporation method. In order to select cells wherein the KU70 gene had been disrupted by homologous recombination, culture was carried out in a puromycin-added McCoy 5A medium (final concentration of puromycin: 0.3 µg/ml), so as to form colonies. The obtained transformed cell colonies were picked up, and cells, wherein either one of two KU70 loci had been disrupted, were selected by the PCR method and the Southern blot analysis.

(2) Gene Disruption with Promoterless Method Vector Plasmid

Subsequently, in order to disrupted either one locus, the linearized pBDTA-Ku70 neo was introduced into the cells by the same above method, and culture was then carried out in a G418-added McCoy 5A medium (final concentration of G418: 300 µg/ml), so as to form colonies. The obtained transformed cells were analyzed by the same method as that in (1) above, so as to select cell strains, wherein the second locus had also been disrupted.

(7) Disruption Efficiency of any Given Gene —HPRT—

In order to examine gene disruption efficiency using human cell line HCT116 or the above human cell line-derived Ku70-disrupted cells, HPRT (hypoxanthine guanine phosphoribosyl transferase) gene disruption was carried out to obtain the above efficiency.

Since HPRT is an enzyme that functions in the salvage pathway of nucleic acid precursor synthesis, even if the HPRT gene is disrupted, it does not affect cell growth. Thus, gene disruption efficiency can accurately be measured using such HPRT. Plasmid DNA used in HPRT gene disruption, which had a hygromycin-resistance gene, was introduced into HCT116 cells and into the HCT116-derived Ku70 disrupted cells. Thereafter, the ratio of the obtained hygromycin-resistance clones, wherein the HPRT gene had been disrupted, was examined by the PCR method and the Southern blotting method.

HPRT gene disruption efficiency (the number of gene-disrupted cells/the number of hygromycin-resistance cells)
Parent strain HCT116: 6/120 (5%)
Ku70-disrupted cell strain: 30/120 (25%)

Thus, since the HPRT gene could be disrupted at an extremely high efficiency, it was shown that the Ku70 gene-disrupted cell strain is a cell strain that is extremely useful for genetic analysis such as gene disruption.

INDUSTRIAL APPLICABILITY

According to the present invention, freely designed DNA can be incorporated into the specific site of the genome of desired cells with high probability. Thus, the present invention provides a gene recombination technique with high accuracy. In addition, since it becomes possible to develop an excision system using Cre/lox, for example, towards unnecessary incorporation possibly occurring during recombination, such unnecessary incorporation can also be eliminated. As a result, a specific gene can reliably be introduced into desired cells, and the gene can stably be expressed therein. Moreover, it is also possible to disrupt a specific gene with reliability. Accordingly, by applying the method of the present invention, a new variety can easily be improved in the field of producing food or the like using microorganisms.

Furthermore, according to the present invention, genes giving disadvantages to industrially applicable living bodies, such as a gene inhibiting matter production or a gene associated with a cytotoxic production system, can easily be eliminated.

Still further, by applying the method of the present invention to higher animals and plants, not only the breeding of the animals and plants, but also the development of a novel technique in the drug discovery and gene therapy in medical field, is anticipated.

REFERENCES

Aronson et al., Mol. Gen. Genet. 242: 490-494. 1994
Ash et al., Mol. Gen. Genet. 221: 37-43. 1990
Ausbel et al., 1987. Current protocols in molecular biology. John Wiley & Sons, New York.
Carter, 1986. Biochem J. 237: 1-7
Critchlow and Jackson, TIBS, 23, 394-398. 1998
Davis et al., Methods Enzymol., 17: 79-143. 1970
Galagan et al., Nature 422: 859-868. 2003
Handa et al., Mol. Gen. Genet. 264, 154-163. 2000
Inoue et al., Mutat. Res., 125: 185-194. 1984
Kuwayama et al., Nucleic Acids Res., 30: E2. 2002
Nickoloff et al., In Nickoloff, J. A. and Hoekstra, M. F. (eds), DNA Damage and Repair. Humana Press, Totowa, N.J., pp. 335-362. 1998
Orbach, M. J. Gene 150: 159-162. 1994
Pall et al., Fungal Genet. Newslett., 40, 59-62. 1993
Sambrook et al., Molecular cloning: A laboratory manual. $2^{nd}$ ed. Cold Spring Harbor Laboratory Press, Cold Spring Harbor, N.Y. 1989
Reiss et al., Proc. Natl. Acad. Sci. USA 97: 3358-3363. 2000
Schroeder et al., Fungal Genet. Newslett. 42, 65-68. 1995
Selker, E. U. Ann. Rev. Genet. 24, 579-613. 1990
Staben et al., Fungal Genet. Newslett., 36: 79-81. 1989
Takita et al., Yeast 13: 763-768. 1997
Tamaru et al., J. Bacteriol. 171: 6288-6293. 1989
Tomita et al., Mol. Gen. Genet., 238: 225-233. 1993
Vollmer et al., Proc. Natl. Acad. Sci. USA 83: 4869-4873. 1986
Wach et al., Yeast 10: 1793-1808. 1994
Walker et al., Nature 412: 607-614. 2001
Wells and Powers. Gene. 34: 315-23. 1985
Wendland et al., Curr. Genet., 44: 115-123. 2003
Yanez and Porter, Nucleic Acids Research., 30: 740-748. 2002
Zoller and Smith 1987. Methods. Enzymol. 154: 329-350

The invention claimed is:

1. A method of conducting homologous recombination, which is characterized in that it comprises the following steps (a) and (b):
   (a) a step of preparing filamentous fungi belonging to genus *Neurospora* or *Aspergillus* wherein a decrease or loss of the functions of a gene selected from the group consisting of KU70, KU80, LIGIV and XRCC4 is induced; and
   (b) a step of introducing foreign DNA into said filamentous fungi, so as to conduct homologous recombination.

2. The method according to claim 1, which is characterized in that said decrease or loss of the functions of the gene is achieved by introducing a mutation or deletion into the gene selected from the group consisting of KU70, KU80, LIGIV and XRCC4.

3. The method according to claim 1, which is characterized in that said decrease or loss of the functions of the gene is achieved by disrupting as a whole the gene selected from the group consisting of KU70, KU80, LIGIV and XRCC4.

4. The method according to claim 1, which is characterized in that said step of introducing foreign DNA is achieved by any one of an electroshock method, a spheroplast method, and a Ti plasmid method.

5. The method according to claim 1, wherein said filamentous fungi belonging to genus *Neurospora* is one type selected from the group consisting of *Neurospora crassa*, *Neurospora silophila*, *Neurospora tetrasperma*, *Neurospora intermedia*, and *Neurospora discreta*.

6. The method according to claim 1, wherein said filamentous fungi belonging to genus *Aspergillus* is one type selected from the group consisting of *Aspergillus oryzae*, *Aspergillus sojae*, *Aspergillus niger*, *Aspergillus awamori*, *Aspergillus kawachi*, *Aspergillus parasiticus*, *Aspergillus flavus*, *Aspergillus nomius*, *Aspergillus fumigatus*, and *Aspergillus nidulans*.

7. Cells of said filamentous fungi obtained by the method of claim 1.

8. Cells of said filamentous fungi obtained by the method of claim 5.

9. Cells of said filamentous fungi obtained by the method of claim 6.

* * * * *

UNITED STATES PATENT AND TRADEMARK OFFICE
CERTIFICATE OF CORRECTION

PATENT NO. : 7,732,208 B2 Page 1 of 1
APPLICATION NO. : 10/590441
DATED : June 8, 2010
INVENTOR(S) : Hirokazu Inoue It is certified that error appears in the above-identified patent and that said Letters Patent is hereby corrected as shown below:

On the title page, Item (54), please delete "CONDUCTING" and insert --INDUCING--.

Signed and Sealed this

Seventeenth Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,732,208 B2  Page 1 of 1
APPLICATION NO. : 10/590441
DATED : June 8, 2010
INVENTOR(S) : Hirokazu Inoue It is certified that error appears in the above-identified patent and that said Letters Patent is hereby corrected as shown below:

On the title page, Item (54) and at Column 1, line 1, in the title, please delete "CONDUCTING" and insert --INDUCING--.

This certificate supersedes the Certificate of Correction issued August 17, 2010.

Signed and Sealed this

Fourteenth Day of September, 2010

David J. Kappos
*Director of the United States Patent and Trademark Office*

SEQUENCE LISTING

```
<160> NUMBER OF SEQ ID NOS: 30

<210> SEQ ID NO 1
<211> LENGTH: 609
<212> TYPE: PRT
<213> ORGANISM: Homo sapiens

<400> SEQUENCE: 1

Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
            20                  25                  30

Ser Gly Arg Asp Ser Leu Ile Phe Leu Val Asp Ala Ser Lys Ala Met
        35                  40                  45
```

```
Phe Glu Ser Gln Ser Glu Asp Glu Leu Thr Pro Phe Asp Met Ser Ile
     50                  55                  60
Gln Cys Ile Gln Ser Val Tyr Ile Ser Lys Ile Ile Ser Ser Asp Arg
 65              70                  75                  80
Asp Leu Leu Ala Val Val Phe Tyr Gly Thr Glu Lys Asp Lys Asn Ser
                 85                  90                  95
Val Asn Phe Lys Asn Ile Tyr Val Leu Gln Glu Leu Asp Asn Pro Gly
             100                 105                 110
Ala Lys Arg Ile Leu Glu Leu Asp Gln Phe Lys Gly Gln Gln Gly Gln
         115                 120                 125
Lys Arg Phe Gln Asp Met Met Gly His Gly Ser Asp Tyr Ser Leu Ser
     130                 135                 140
Glu Val Leu Trp Val Cys Ala Asn Leu Phe Ser Asp Val Gln Phe Lys
145                 150                 155                 160
Met Ser His Lys Arg Ile Met Leu Phe Thr Asn Glu Asp Asn Pro His
             165                 170                 175
Gly Asn Asp Ser Ala Lys Ala Ser Arg Ala Arg Thr Lys Ala Gly Asp
             180                 185                 190
Leu Arg Asp Thr Gly Ile Phe Leu Asp Leu Met His Leu Lys Lys Pro
         195                 200                 205
Gly Gly Phe Asp Ile Ser Leu Phe Tyr Arg Asp Ile Ile Ser Ile Ala
     210                 215                 220
Glu Asp Glu Asp Leu Arg Val His Phe Glu Glu Ser Ser Lys Leu Glu
225                 230                 235                 240
Asp Leu Leu Arg Lys Val Arg Ala Lys Glu Thr Arg Lys Arg Ala Leu
             245                 250                 255
Ser Arg Leu Lys Leu Lys Leu Asn Lys Asp Ile Val Ile Ser Val Gly
         260                 265                 270
Ile Tyr Asn Leu Val Gln Lys Ala Leu Lys Pro Pro Ile Lys Leu
     275                 280                 285
Tyr Arg Glu Thr Asn Glu Pro Val Lys Thr Lys Thr Arg Thr Phe Asn
     290                 295                 300
Thr Ser Thr Gly Gly Leu Leu Leu Pro Ser Asp Thr Lys Arg Ser Gln
305                 310                 315                 320
Ile Tyr Gly Ser Arg Gln Ile Ile Leu Glu Lys Glu Glu Thr Glu Glu
             325                 330                 335
Leu Lys Arg Phe Asp Asp Pro Gly Leu Met Leu Met Gly Phe Lys Pro
         340                 345                 350
Leu Val Leu Leu Lys Lys His His Tyr Leu Arg Pro Ser Leu Phe Val
     355                 360                 365
Tyr Pro Glu Glu Ser Leu Val Ile Gly Ser Ser Thr Leu Phe Ser Ala
 370                 375                 380
Leu Leu Ile Lys Cys Leu Glu Lys Glu Val Ala Ala Leu Cys Arg Tyr
385                 390                 395                 400
Thr Pro Arg Arg Asn Ile Pro Pro Tyr Phe Val Ala Leu Val Pro Gln
             405                 410                 415
Glu Glu Glu Leu Asp Asp Gln Lys Ile Gln Val Thr Pro Pro Gly Phe
         420                 425                 430
Gln Leu Val Phe Leu Pro Phe Ala Asp Asp Lys Arg Lys Met Pro Phe
     435                 440                 445
Thr Glu Lys Ile Met Ala Thr Pro Glu Gln Val Gly Lys Met Lys Ala
 450                 455                 460
Ile Val Glu Lys Leu Arg Phe Thr Tyr Arg Ser Asp Ser Phe Glu Asn
```

```
                465                 470                 475                 480
    Pro Val Leu Gln Gln His Phe Arg Asn Leu Glu Ala Leu Ala Leu Asp
                    485                 490                 495
    Leu Met Glu Pro Glu Gln Ala Val Asp Leu Thr Leu Pro Lys Val Glu
                    500                 505                 510
    Ala Met Asn Lys Arg Leu Gly Ser Leu Val Asp Glu Phe Lys Glu Leu
                    515                 520                 525
    Val Tyr Pro Pro Asp Tyr Asn Pro Glu Gly Lys Val Thr Lys Arg Lys
                    530                 535                 540
    His Asp Asn Glu Gly Ser Gly Ser Lys Arg Pro Lys Val Glu Tyr Ser
    545                 550                 555                 560
    Glu Glu Glu Leu Lys Thr His Ile Ser Lys Gly Thr Leu Gly Lys Phe
                    565                 570                 575
    Thr Val Pro Met Leu Lys Glu Ala Cys Arg Ala Tyr Gly Leu Lys Ser
                    580                 585                 590
    Gly Leu Lys Lys Gln Glu Leu Leu Glu Ala Leu Thr Lys His Phe Gln
                    595                 600                 605
    Asp

<210> SEQ ID NO 2
<211> LENGTH: 732
<212> TYPE: PRT
<213> ORGANISM: Homo sapiens

<400> SEQUENCE: 2

Met Val Arg Ser Gly Asn Lys Ala Ala Val Val Leu Cys Met Asp Val
1               5                   10                  15
Gly Phe Thr Met Ser Asn Ser Ile Pro Gly Ile Glu Ser Pro Phe Glu
                20                  25                  30
Gln Ala Lys Lys Val Ile Thr Met Phe Val Gln Arg Gln Val Phe Ala
                35                  40                  45
Glu Asn Lys Asp Glu Ile Ala Leu Val Leu Phe Gly Thr Asp Gly Thr
            50                  55                  60
Asp Asn Pro Leu Ser Gly Gly Asp Gln Tyr Gln Asn Ile Thr Val His
65                  70                  75                  80
Arg His Leu Met Leu Pro Asp Phe Asp Leu Leu Glu Asp Ile Glu Ser
                85                  90                  95
Lys Ile Gln Pro Gly Ser Gln Gln Ala Asp Phe Leu Asp Ala Leu Ile
                100                 105                 110
Val Ser Met Asp Val Ile Gln His Glu Thr Ile Gly Lys Lys Phe Glu
            115                 120                 125
Lys Arg His Ile Glu Ile Phe Thr Asp Leu Ser Ser Arg Phe Ser Lys
        130                 135                 140
Ser Gln Leu Asp Ile Ile Ile His Ser Leu Lys Lys Cys Asp Ile Ser
145                 150                 155                 160
Leu Gln Phe Phe Leu Pro Phe Ser Leu Gly Lys Glu Asp Gly Ser Gly
                165                 170                 175
Asp Arg Gly Asp Gly Pro Phe Arg Leu Gly Gly His Gly Pro Ser Phe
            180                 185                 190
Pro Leu Lys Gly Ile Thr Glu Gln Gln Lys Glu Gly Leu Glu Ile Val
        195                 200                 205
Lys Met Val Met Ile Ser Leu Glu Gly Glu Asp Gly Leu Asp Glu Ile
    210                 215                 220
Tyr Ser Phe Ser Glu Ser Leu Arg Lys Leu Cys Val Phe Lys Lys Ile
```

-continued

```
            225                 230                 235                 240
        Glu Arg His Ser Ile His Trp Pro Cys Arg Leu Thr Ile Gly Ser Asn
                        245                 250                 255
        Leu Ser Ile Arg Ile Ala Ala Tyr Lys Ser Ile Leu Gln Glu Arg Val
                        260                 265                 270
        Lys Lys Thr Trp Thr Val Val Asp Ala Lys Thr Leu Lys Lys Glu Asp
                        275                 280                 285
        Ile Gln Lys Glu Thr Val Tyr Cys Leu Asn Asp Asp Glu Thr Glu
                        290                 295                 300
        Val Leu Lys Glu Asp Ile Ile Gln Gly Phe Arg Tyr Gly Ser Asp Ile
        305                 310                 315                 320
        Val Pro Phe Ser Lys Val Asp Glu Gln Met Lys Tyr Lys Ser Glu
                        325                 330                 335
        Gly Lys Cys Phe Ser Val Leu Gly Phe Cys Lys Ser Ser Gln Val Gln
                        340                 345                 350
        Arg Arg Phe Phe Met Gly Asn Gln Val Leu Lys Val Phe Ala Ala Arg
                        355                 360                 365
        Asp Asp Glu Ala Ala Val Ala Leu Ser Ser Leu Ile His Ala Leu
                        370                 375                 380
        Asp Asp Leu Asp Met Val Ala Ile Val Arg Tyr Ala Tyr Asp Lys Arg
        385                 390                 395                 400
        Ala Asn Pro Gln Val Gly Val Ala Phe Pro His Ile Lys His Asn Tyr
                        405                 410                 415
        Glu Cys Leu Val Tyr Val Gln Leu Pro Phe Met Glu Asp Leu Arg Gln
                        420                 425                 430
        Tyr Met Phe Ser Ser Leu Lys Asn Ser Lys Lys Tyr Ala Pro Thr Glu
                        435                 440                 445
        Ala Gln Leu Asn Ala Val Asp Ala Leu Ile Asp Ser Met Ser Leu Ala
                        450                 455                 460
        Lys Lys Asp Glu Lys Thr Asp Thr Leu Glu Asp Leu Phe Pro Thr Thr
        465                 470                 475                 480
        Lys Ile Pro Asn Pro Arg Phe Gln Arg Leu Phe Gln Cys Leu Leu His
                        485                 490                 495
        Arg Ala Leu His Pro Arg Glu Pro Leu Pro Ile Gln Gln His Ile
                        500                 505                 510
        Trp Asn Met Leu Asn Pro Pro Ala Glu Val Thr Thr Lys Ser Gln Ile
                        515                 520                 525
        Pro Leu Ser Lys Ile Lys Thr Leu Phe Pro Leu Ile Glu Ala Lys Lys
                        530                 535                 540
        Lys Asp Gln Val Thr Ala Gln Glu Ile Phe Gln Asp Asn His Glu Asp
        545                 550                 555                 560
        Gly Pro Thr Ala Lys Lys Leu Lys Thr Glu Gln Gly Gly Ala His Phe
                        565                 570                 575
        Ser Val Ser Ser Leu Ala Glu Gly Ser Val Thr Ser Val Gly Ser Val
                        580                 585                 590
        Asn Pro Ala Glu Asn Phe Arg Val Leu Val Lys Gln Lys Lys Ala Ser
                        595                 600                 605
        Phe Glu Glu Ala Ser Asn Gln Leu Ile Asn His Ile Glu Gln Phe Leu
                        610                 615                 620
        Asp Thr Asn Glu Thr Pro Tyr Phe Met Lys Ser Ile Asp Cys Ile Arg
        625                 630                 635                 640
        Ala Phe Arg Glu Glu Ala Ile Lys Phe Ser Glu Glu Gln Arg Phe Asn
                        645                 650                 655
```

```
Asn Phe Leu Lys Ala Leu Gln Glu Lys Val Glu Ile Lys Gln Leu Asn
            660                 665                 670
His Phe Trp Glu Ile Val Val Gln Asp Gly Ile Thr Leu Ile Thr Lys
        675                 680                 685
Glu Glu Ala Ser Gly Ser Ser Val Thr Ala Glu Glu Ala Lys Lys Phe
    690                 695                 700
Leu Ala Pro Lys Asp Lys Pro Ser Gly Asp Thr Ala Ala Val Phe Glu
705                 710                 715                 720
Glu Gly Gly Asp Val Asp Asp Leu Leu Asp Met Ile
                725                 730

<210> SEQ ID NO 3
<211> LENGTH: 645
<212> TYPE: PRT
<213> ORGANISM: Neurospora crassa

<400> SEQUENCE: 3

Met Ser Trp Arg Lys Asp Gln Asp Glu Arg Leu Asp Gly Asp Glu Gly
1               5                   10                  15
Asp Glu Glu Leu Asp Glu Asn Val Ser Tyr His Gln Ser Thr His Val
            20                  25                  30
Leu Phe Ala Ile Asp Val Ser Lys Ser Met Leu Lys Pro Pro Gln Asn
        35                  40                  45
Thr Gly Asp Lys Lys Ala Asp Lys Asp Ser Ala Leu Thr Ala Ala Leu
    50                  55                  60
Thr Cys Ala Tyr Gln Ile Met Gln Gln Arg Ile Ile Ser Gln Pro Lys
65                  70                  75                  80
Asp Met Met Gly Val Leu Leu Phe Gly Thr Glu Lys Ser Lys Phe Arg
                85                  90                  95
Asp Asp Ser Gly Asn Gly Thr Gly Tyr Pro His Cys Tyr Leu Leu Ser
            100                 105                 110
Asp Leu Asp Ile Pro Gly Ala Glu Asp Val Lys Lys Leu Lys Ala Leu
        115                 120                 125
Ile Glu Asp Gly Asp Asp Glu Asp Glu Ile Met Val Pro Ser Lys Glu
    130                 135                 140
Pro Val Ile Met Ser Asn Met Leu Phe Cys Ala Asn Gln Val Phe Thr
145                 150                 155                 160
Thr Asn Ala Ala Asn Phe Gly Ser Arg Arg Leu Phe Ile Val Thr Asp
                165                 170                 175
Asn Asp Asp Pro His Ala Gly Asp Lys Gln Ala Lys Ser Ser Ala Ala
            180                 185                 190
Val Arg Ala Lys Asp Leu Tyr Asp Leu Gly Val Val Ile Glu Leu Phe
        195                 200                 205
Pro Ile Ser Arg Glu Asp Lys Lys Phe Asp Leu Ser Lys Phe Tyr Asp
    210                 215                 220
Asp Ile Ile Tyr Arg Asn Pro Ala Ala Glu Ala Gly Gln Ser Glu Ser
225                 230                 235                 240
Pro Lys Thr Ser Lys Ser Gly Asp Gly Leu Thr Leu Leu Asn Ser Leu
                245                 250                 255
Ile Ser Asn Ile Asn Ser Lys Gln Thr Pro Lys Arg Ser Tyr Phe Ser
            260                 265                 270
Asn Leu Pro Phe Glu Leu Ala Pro Gly Leu Thr Ile Ser Ile Lys Gly
        275                 280                 285
Tyr Met Pro Leu Asn Arg Gln Thr Pro Thr Arg Ser Cys Tyr Val Tyr
```

```
            290                 295                 300
Glu Gly Glu Glu Gln Ala Gln Val Val Gln Ser Glu Thr Ala Gln Val
305                 310                 315                 320

Asp Phe Ala Ala Arg Thr Val Glu Lys Ser Glu Leu Arg Lys Gly Tyr
                325                 330                 335

Lys Phe Gly Gly Glu His Ile Cys Phe Lys Pro Glu Glu Leu Ala Glu
            340                 345                 350

Leu Lys Gln Met Gly Lys Lys Thr Leu Arg Ile Ile Gly Phe Lys Lys
        355                 360                 365

Arg Ser Lys Ile Pro Ser Trp Ala Ser Val Lys Ser Ile Phe Ile
370                 375                 380

Phe Pro Ser Glu Glu Gln Tyr Val Gly Ser Thr Arg Val Phe Ser Ala
385                 390                 395                 400

Leu Trp Gln Lys Leu Leu Lys Asp Asp Lys Val Gly Ile Ala Trp Phe
                405                 410                 415

Val Ala Arg Glu Asn Ala His Pro Val Met Val Ala Ile Phe Pro Ser
                420                 425                 430

Gly Asn Pro Asp Asp Glu Glu Ala Asn Thr Pro Tyr Leu Pro Ala Gly
            435                 440                 445

Leu Trp Leu Tyr Pro Leu Pro Phe Ala Asp Asp Val Arg Ser Val Asp
        450                 455                 460

His Val Thr Ala Pro Pro Arg Pro Ala Asp Glu Leu Thr Asp Gln Met
465                 470                 475                 480

Arg Gln Val Ile Gln Asn Leu Gln Leu Pro Lys Ala Met Tyr Asp Pro
                485                 490                 495

Arg Lys Tyr Pro Asn Pro Ser Leu Gln Trp His Tyr Lys Ile Leu Gln
            500                 505                 510

Ala Lys Ala Leu Asp Glu Glu Thr Pro Asp Ala Met Asp Asp Val Thr
        515                 520                 525

Leu Pro Lys Tyr Arg Gln Ile Asp Lys Arg Val Gly Gly Tyr Leu Ala
    530                 535                 540

Glu Trp Lys Glu Met Leu Ala Lys Lys Ala Asn Asp Leu Gln Asn Thr
545                 550                 555                 560

Arg Ala Phe Lys Arg Glu Phe Glu Glu Asp Asp Glu Arg Pro Ala Lys
                565                 570                 575

Arg Ala Lys Pro Ser Lys Lys Ala Ala Ser Gly Gly Gly Pro Ala
            580                 585                 590

Asn Ser Asn Ala Asp Leu Lys Lys Ala Phe Glu Gln Gly Thr Leu Gly
        595                 600                 605

Lys Met Thr Val Ala Glu Leu Lys Asp Ile Met Ala Ser Lys Gly Ile
    610                 615                 620

Ser Thr Ala Gly Arg Lys Ala Glu Leu Val Glu Arg Leu Glu Gln Trp
625                 630                 635                 640

Val Glu Glu Asn Leu
                645

<210> SEQ ID NO 4
<211> LENGTH: 661
<212> TYPE: PRT
<213> ORGANISM: Neurospora crassa

<400> SEQUENCE: 4

Met Ala Asp Lys Glu Ala Thr Val Tyr Val Ile Asp Leu Gly Glu Ser
1               5                   10                  15
```

```
Met Ala Asp Cys His Asn Gly Arg Asn Glu Ser Asp Leu Glu Phe Gly
             20                  25                  30

Met Arg Tyr Ile Trp Asp Lys Ile Thr Thr Val Ala Ala Ser Arg
         35                  40                  45

Lys Thr Trp Asn Val Gly Val Gly Leu Asn Thr Asp Glu Thr Asn
 50                  55                  60

Asn Asn Glu Asn Arg Glu Glu Tyr Gln Gly Tyr Glu Asn Ile Ser Val
 65                  70                  75                  80

Leu Gln Glu Leu Gly Pro Met Thr Met Ala Ser Leu Arg Ala Leu Lys
                 85                  90                  95

Ser Lys Ile Glu Pro Ser Ser Thr Ser Ser Ala Asp Ala Ile Ser Ala
                100                 105                 110

Ile Val Val Ala Leu Arg Met Ile Gln Thr Phe Thr Lys Lys Leu Lys
                115                 120                 125

Tyr Lys Arg Lys Ile Ile Val Val Thr Asn Gly Glu Ser Pro Ile Asp
 130                 135                 140

Asp Asp Gln Ser Glu Glu Val Ala Asn Met Leu Asn Asp Val Gly Ile
145                 150                 155                 160

Glu Leu Ile Val Leu Gly Val Asp Phe Asp Asp Ala Glu Tyr Gly Phe
                165                 170                 175

Lys Glu Glu Asp Lys Pro Arg His Lys Glu Gln Asn Gly Lys Ile Leu
                180                 185                 190

Lys Thr Leu Val Asp His Cys Glu Ser Gly Ala Phe Gly Thr Met Ala
                195                 200                 205

Gln Ala Val Glu Glu Leu Ala Thr Pro Arg Ile Lys Ser Val Arg Pro
 210                 215                 220

Phe Lys Ala Tyr Asp Gly Pro Leu Thr Leu Gly Asp Pro Gln Lys Tyr
225                 230                 235                 240

Pro Ser Ala Leu Ser Ile Gln Val Glu Arg Tyr Phe Lys Thr Lys Arg
                245                 250                 255

Ala Thr Pro Pro Ser Ala Ser Asn Val Ala Asn Pro Asn Gly Pro Pro
                260                 265                 270

Gln Thr Gln Val Trp Asn Glu Asp Gly Val Pro Phe Ser Gly Val
                275                 280                 285

Gly Leu Gln Pro Val Lys Gln Leu Arg Thr Tyr Arg Ile Glu Asp Ser
 290                 295                 300

Lys Ala Ala Gly Gly Lys Lys Asp Val Asp Met Glu Asp Leu Ala Lys
305                 310                 315                 320

Ala Tyr Gln Tyr Gly Arg Thr Val Val Pro Phe Gly Lys Ser Glu Glu
                325                 330                 335

Asp Tyr Leu Lys Tyr Glu Thr Thr Lys Ser Phe Thr Ile Ile Gly Phe
                340                 345                 350

Val Pro Met Ser Ser Tyr Glu Pro Phe Leu Asn Met Gly Glu Thr Gly
                355                 360                 365

Leu Ile Val Ala Gln Lys Val Asn Glu Glu Ala Glu Leu Gly Leu Ser
 370                 375                 380

Ala Leu Ile His Ala Leu His Glu Leu Glu Ser Tyr Ala Val Ala Arg
385                 390                 395                 400

Tyr Val Asn Lys Asp Lys Ala Pro Pro Gln Ile Leu Leu Leu Lys Pro
                405                 410                 415

Asn Pro Ala Ile Glu Asp Asp Ile Glu Cys Leu Tyr Asp Ile Pro Leu
                420                 425                 430

Pro Phe Ala Glu Asp Val Arg Ser Tyr Gln Phe Pro Pro Leu Asp Lys
```

-continued

```
                435                 440                 445
Val Leu Thr Ile Thr Gly Asn Val Leu Thr Glu His Arg Leu Leu Pro
    450                 455                 460
Asn Asn Asp Leu Gln Gln Ala Met Ser Asp Tyr Val Asp Ala Met Asp
465                 470                 475                 480
Leu Thr Glu Tyr Gly Gln Asp Asp Gly His Pro Ala Glu Tyr Ala
                485                 490                 495
Pro Ile Asp Asp Leu Tyr Asn Pro Val Ile His His Met Asn Gln Ala
                500                 505                 510
Ile Arg Asn Arg Ala Val Asn Pro Asp Ala Pro Leu Pro Pro Val Ala
                515                 520                 525
Glu Ile Leu Thr Arg Phe Thr His Pro Pro Glu Pro Leu Leu Ala Lys
    530                 535                 540
Ala Lys Thr Glu Ile Asp Gly Leu Ile Gln Ala Ala Glu Val Lys Lys
545                 550                 555                 560
Ala Glu Asp Asp Glu Thr Ile Glu Ile Ala Ala Lys Gln Met Gly Asn
                565                 570                 575
Ile Ile Cys Lys Leu Val Ser Asp Ser Phe Ala Asp Val Leu Tyr Pro
                580                 585                 590
Arg Ala Ala Glu Asn Leu Arg Val Met Arg Glu Glu Leu Ile Asn Met
    595                 600                 605
Glu Val Pro Thr Leu Tyr Asn Lys Tyr Ile Thr Lys Leu Lys Glu Ser
    610                 615                 620
Leu Leu Ser Val Ser Glu Ser Lys Ser Met Gly Gly Ser Leu Thr Gly
625                 630                 635                 640
Ser Gly Glu Asp Thr Asp Glu Glu Arg Gln Arg Lys His Pro Phe Ser
                645                 650                 655
Ala Gln Glu Val Gly
        660

<210> SEQ ID NO 5
<211> LENGTH: 25
<212> TYPE: DNA
<213> ORGANISM: Artificial
<220> FEATURE:
<223> OTHER INFORMATION: Designed nucleotides

<400> SEQUENCE: 5
gtgctgtagc cgttttgggt atcgc                                        25

<210> SEQ ID NO 6
<211> LENGTH: 34
<212> TYPE: DNA
<213> ORGANISM: Artificial
<220> FEATURE:
<223> OTHER INFORMATION: Designed nucleotides

<400> SEQUENCE: 6
ggcgtaatag cgaagagata gttgctggaa ataa                              34

<210> SEQ ID NO 7
<211> LENGTH: 33
<212> TYPE: DNA
<213> ORGANISM: Artificial
<220> FEATURE:
<223> OTHER INFORMATION: Designed nucleotides

<400> SEQUENCE: 7
aagcataaag tgtaaaggct tgttgatgac cgt                               33
```

<210> SEQ ID NO 8
<211> LENGTH: 25
<212> TYPE: DNA
<213> ORGANISM: Artificial
<220> FEATURE:
<223> OTHER INFORMATION: Designed nucleotides

<400> SEQUENCE: 8
ttggacgccg cacacctctc gctct                                    25

<210> SEQ ID NO 9
<211> LENGTH: 34
<212> TYPE: DNA
<213> ORGANISM: Artificial
<220> FEATURE:
<223> OTHER INFORMATION: Designed nucleotides

<400> SEQUENCE: 9
ttatttccag caactatctc ttcgctatta cgcc                          34

<210> SEQ ID NO 10
<211> LENGTH: 34
<212> TYPE: DNA
<213> ORGANISM: Artificial
<220> FEATURE:
<223> OTHER INFORMATION: Designed nucleotides

<400> SEQUENCE: 10
cacggtcatc aacaagcctt tacactttat gctt                          34

<210> SEQ ID NO 11
<211> LENGTH: 25
<212> TYPE: DNA
<213> ORGANISM: Artificial
<220> FEATURE:
<223> OTHER INFORMATION: Designed nucleotides

<400> SEQUENCE: 11
gcgccgggag gttgttcgta agctg                                    25

<210> SEQ ID NO 12
<211> LENGTH: 34
<212> TYPE: DNA
<213> ORGANISM: Artificial
<220> FEATURE:
<223> OTHER INFORMATION: Designed nucleotides

<400> SEQUENCE: 12
ggcgtaatag cgaagaggct tttcggcttt gctg                          34

<210> SEQ ID NO 13
<211> LENGTH: 34
<212> TYPE: DNA
<213> ORGANISM: Artificial
<220> FEATURE:
<223> OTHER INFORMATION: Designed nucleotides

<400> SEQUENCE: 13
aagcataaag tgtaaagcag ggttggagac aggt                          34

<210> SEQ ID NO 14
<211> LENGTH: 25
<212> TYPE: DNA
<213> ORGANISM: Artificial
<220> FEATURE:

```
<223> OTHER INFORMATION: Designed nucleotides

<400> SEQUENCE: 14
aaggcggagt tgttggctgc gaagg                                          25

<210> SEQ ID NO 15
<211> LENGTH: 34
<212> TYPE: DNA
<213> ORGANISM: Artificial
<220> FEATURE:
<223> OTHER INFORMATION: Designed nucleotides

<400> SEQUENCE: 15
cagcaaagcc gaaaagcctc ttcgctatta cgcc                                34

<210> SEQ ID NO 16
<211> LENGTH: 34
<212> TYPE: DNA
<213> ORGANISM: Artificial
<220> FEATURE:
<223> OTHER INFORMATION: Designed nucleotides

<400> SEQUENCE: 16
acctgtctcc aaccctgctt tacactttat gctt                                34

<210> SEQ ID NO 17
<211> LENGTH: 25
<212> TYPE: DNA
<213> ORGANISM: Artificial
<220> FEATURE:
<223> OTHER INFORMATION: Designed nucleotides

<400> SEQUENCE: 17
gagaactgat catgcgatgc gtggc                                          25

<210> SEQ ID NO 18
<211> LENGTH: 25
<212> TYPE: DNA
<213> ORGANISM: Artificial
<220> FEATURE:
<223> OTHER INFORMATION: Designed nucleotides

<400> SEQUENCE: 18
cattcgcttg atcgacatgg ttggc                                          25

<210> SEQ ID NO 19
<211> LENGTH: 29
<212> TYPE: DNA
<213> ORGANISM: Artificial
<220> FEATURE:
<223> OTHER INFORMATION: Designed nucleotides

<400> SEQUENCE: 19
cacattgtcc aagcttactg tggctaccc                                      29

<210> SEQ ID NO 20
<211> LENGTH: 29
<212> TYPE: DNA
<213> ORGANISM: Artificial
<220> FEATURE:
<223> OTHER INFORMATION: Designed nucleotides

<400> SEQUENCE: 20
gggtagccac agtaagcttg gacaatgtg                                      29
```

```
<210> SEQ ID NO 21
<211> LENGTH: 29
<212> TYPE: DNA
<213> ORGANISM: Artificial
<220> FEATURE:
<223> OTHER INFORMATION: Designed nucleotides

<400> SEQUENCE: 21
cacattgtcc aagcttactg tggctaccc                                29

<210> SEQ ID NO 22
<211> LENGTH: 29
<212> TYPE: DNA
<213> ORGANISM: Artificial
<220> FEATURE:
<223> OTHER INFORMATION: Designed nucleotides

<400> SEQUENCE: 22
gggtagccac agtaagcttg acaatgtg                                 29

<210> SEQ ID NO 23
<211> LENGTH: 41
<212> TYPE: DNA
<213> ORGANISM: Artificial
<220> FEATURE:
<223> OTHER INFORMATION: Designed nucleotides

<400> SEQUENCE: 23
gctataggcg cgcctctgca tttaaggaga gaatagctgt g                  41

<210> SEQ ID NO 24
<211> LENGTH: 41
<212> TYPE: DNA
<213> ORGANISM: Artificial
<220> FEATURE:
<223> OTHER INFORMATION: Designed nucleotides

<400> SEQUENCE: 24
agaacagcgg ccgcaagaga tctcgatcac tgcttatgat c                  41

<210> SEQ ID NO 25
<211> LENGTH: 40
<212> TYPE: DNA
<213> ORGANISM: Artificial
<220> FEATURE:
<223> OTHER INFORMATION: Designed nucleotides

<400> SEQUENCE: 25
ctttaggcgg ccgcaattca agatgagtca taagaggatc                    40

<210> SEQ ID NO 26
<211> LENGTH: 37
<212> TYPE: DNA
<213> ORGANISM: Artificial
<220> FEATURE:
<223> OTHER INFORMATION: Designed nucleotides

<400> SEQUENCE: 26
catgtcgaca tttcaagaca ggtgaagagg tgacaag                       37

<210> SEQ ID NO 27
<211> LENGTH: 39
<212> TYPE: DNA
<213> ORGANISM: Artificial
<220> FEATURE:
<223> OTHER INFORMATION: Designed nucleotides
```

-continued

```
<400> SEQUENCE: 27
gctatagtcg actctgcatt taaggagaga atagctgtg                    39

<210> SEQ ID NO 28
<211> LENGTH: 41
<212> TYPE: DNA
<213> ORGANISM: Artificial
<220> FEATURE:
<223> OTHER INFORMATION: Designed nucleotides

<400> SEQUENCE: 28
agaacagcgg ccgcaagaga tctcgatcac tgcttatgat c                 41

<210> SEQ ID NO 29
<211> LENGTH: 40
<212> TYPE: DNA
<213> ORGANISM: Artificial
<220> FEATURE:
<223> OTHER INFORMATION: Designed nucleotides

<400> SEQUENCE: 29
ctttaggcgg ccgcaattca agatgagtca taagaggatc                   40

<210> SEQ ID NO 30
<211> LENGTH: 40
<212> TYPE: DNA
<213> ORGANISM: Artificial
<220> FEATURE:
<223> OTHER INFORMATION: Designed nucleotides

<400> SEQUENCE: 30
atcgcaggcg cgccagacag gtgaagaggt gacaagatac                   40
```